(12) United States Patent
Kitade et al.

(10) Patent No.: US 8,633,304 B2
(45) Date of Patent: Jan. 21, 2014

(54) OLIGONUCLEOTIDE DERIVATIVE COMPRISING AN AROMATIC COMPOUND

(75) Inventors: Yukio Kitade, Gifu (JP); Yoshiaki Kitamura, Gifu (JP)

(73) Assignee: Gifu University, Gifu-Shi (JP)

( * ) Notice: Subject to any disclaimer, the term of this patent is extended or adjusted under 35 U.S.C. 154(b) by 0 days.

(21) Appl. No.: 13/514,547

(22) PCT Filed: Dec. 8, 2010

(86) PCT No.: PCT/JP2010/072020
§ 371 (c)(1),
(2), (4) Date: Jun. 7, 2012

(87) PCT Pub. No.: WO2011/071078
PCT Pub. Date: Jun. 16, 2011

(65) Prior Publication Data
US 2012/0245341 A1    Sep. 27, 2012

(30) Foreign Application Priority Data
Dec. 8, 2009 (JP) ................................. 2009-278456

(51) Int. Cl.
*C07H 21/02* (2006.01)
*C07H 21/04* (2006.01)

(52) U.S. Cl.
USPC .................... 536/23.1; 536/24.5; 536/24.3

(58) Field of Classification Search
None
See application file for complete search history.

(56) References Cited

FOREIGN PATENT DOCUMENTS

WO    WO 2007/094135 A1    8/2007

OTHER PUBLICATIONS

Agrawal et al., "Antisense and/or Immunostimulatory Oligonucleotide Therapeutics", Current Cancer Drug Targets, vol. 1, 2001, pp. 197-209.
Beigelman et al, "Chemical Modification of Hammerhead Ribozymes", Catalytic Activity and Nuclease Resistance, The Journal of Biological Chemistry, vol. 270, No. 43, Issue of Oct. 27, 1995, pp. 25702-25708.
Hohjoh, "RNA interference (RNAi) Induction with various types of synthetic oligonucleotide duplexes in cultured human cells", FEBS Letters 521, 2002. pp. 195-199.
International Search Report issued in PCT/JP2010/072020 dated Feb. 8, 2011.
Lee et al., "C3-Symmetric metacyclophane-based anion receptors with three thiourea groups as linkers between aromatic groups", Tetrahedron Letters, 2000, vol. 41, No. 32, pp. 6083-6087.
Leung et al., "Effect of spacer geometry on oxoanion binding by bis- and tetrakis-thiourea hosts", Tetrahedron, 2008, vol. 64, No. 11, pp. 2530-2536.
Ragusa et al., "A Combined Computational and Experimental Approach for the Analysis of the Enantioselective Potential of a New Macrocyclic Receptor for N-Protected a-Amino Acids", DOI: 10.1002/chem.200601289, Chem. Eur. J. 2007, vol. 13, pp. 2717-2728.
Smith et al., "Solid and Solution Phase Organic Syntheses of Oligomeric Thioureas", Journal of Organic Chemistry, 1996, vol. 61, No. 25, pp. 8811-8818.
Ueno et al., "Synthesis of novel siRNAs having thymidine dimers consisting of a carbamate or a urea linkage at their 3' overhang regions and their ability to suppress human RNase L protein expression", Biochemical and Biophysical Research Communications, vol. 330 (2005) pp. 1168-1175.
Zinnen et al., "Selection, design, and characterization of a new potentially therapeutic ribozyme", RNA 2002 8: p. 214-228.

*Primary Examiner* — Richard Schnizer
(74) *Attorney, Agent, or Firm* — Birch, Stewart, Kolasch & Birch, LLP

(57) ABSTRACT

The present invention provides an oligonucleotide derivative that enables to easily synthesize an oligonucleotide derivative chemically modified at the 3'-end with two moieties each having a benzene or pyridine structure with a few steps, an aromatic compound serving as a precursor for preparing the modification carrier for synthesizing oligonucleotide derivative, and the oligonucleotide derivative and the oligonucleotide construct using the same, that is chemically modified at the 3'-end with two moieties each having a benzene or pyridine structure, and has good permeability through a cell membrane and excellent nuclease resistance. The modification carrier for synthesizing oligonucleotide derivative, comprising a unit and a carrier carrying the unit directly or via a linker, wherein the unit is represented by the formula (a): wherein, $R_1$ to $R_6$ each independently represent hydrogen or a substituent other than hydrogen; $Z^1$ and $Z^2$ each independently represent CH or nitrogen; and X represents oxygen or sulfur.

(a)

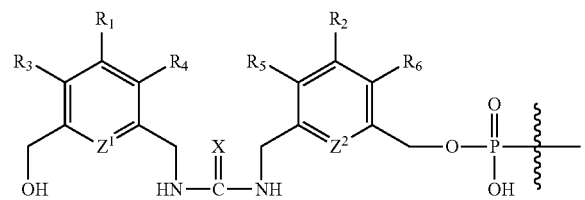

11 Claims, 7 Drawing Sheets

BuP =

BP =

```
                            SEQUENCE LISTING

<160> NUMBER OF SEQ ID NOS: 3

<210> SEQ ID NO 1
<211> LENGTH: 19
<212> TYPE: RNA
<213> ORGANISM: Artificial Sequence
<220> FEATURE:
<223> OTHER INFORMATION: antisense strand of siRNA
<220> FEATURE:
<221> NAME/KEY: modified_base
<222> LOCATION: (19)..(19)

<400> SEQUENCE: 1
guaggaguag ugaaaggcc                                                  19

<210> SEQ ID NO 2
<211> LENGTH: 19
<212> TYPE: RNA
<213> ORGANISM: Artificial Sequence
<220> FEATURE:
<223> OTHER INFORMATION: sense strand of siRNA
<220> FEATURE:
<221> NAME/KEY: modified_base
<222> LOCATION: (19)..(19)

<400> SEQUENCE: 2
ggccuuucac uacuccuac                                                  19

<210> SEQ ID NO 3
<211> LENGTH: 19
<212> TYPE: RNA
<213> ORGANISM: Artificial Sequence
<220> FEATURE:
<223> OTHER INFORMATION: antisense strand of siRNA
<220> FEATURE:
<221> NAME/KEY: modified_base
<222> LOCATION: (19)..(19)

<400> SEQUENCE: 3
guaggaguag ugaaaggcc                                                  19
```

OLIGONUCLEOTIDE DERIVATIVE COMPRISING AN AROMATIC COMPOUND

FIELD OF THE INVENTION

The present invention relates to an aromatic compound, a urea-containing modification carrier for synthesizing an oligonucleotide derivative using the same, an oligonucleotide derivative, and an oligonucleotide construct.

BACKGROUND OF THE INVENTION

Various oligonucleotides such as DNA and RNA have recently expanded their applications in the fields of treatment and diagnosis. Examples of the diagnostic application include DNA chip and DNA microarray. Examples of the therapeutic application include introduction of therapeutic gene and disease-related gene silencing by knockdown thereof. There are also attempts to use aptamers, which are nucleic acid or peptide molecules that specifically bind to a target molecule, as a therapeutic agent.

One of the especially interesting nucleic-acid technologies is a target gene knockdown technique by RNA interference (RNAi). RNAi is a process of silencing the activity of a gene by the action of a double-stranded RNA (dsRNA) molecule having the homologous sequence to the gene. In gene silencing by RNAi, the dsRNA molecule is recognized by Dicer which is one of the enzymes in the RNase III family and cut into small fragments called siRNAs (short interfering RNAs) of about 21 to 23 nucleotides long, an siRNA is incorporated into the RISC(RNA-induced silencing complex), and a homologous mRNA to the incorporated siRNA is cleaved at the center and degraded.

The knockdown technique however has problems of insufficient expression and difficulty in stable expression of an intended knockdown effect, because exogenous DNAs and RNAs are exposed to various nucleases in living organisms and RNAs are particularly sensitive to nuclease degradation.

To solve such a problem, chemical modifications on oligonucleotides have been studied for increasing nuclease resistance of oligonucleotides (Non-patent Documents 1 to 3). For example, an siRNA molecule has been attempted to be chemically modified with various substituents at a sugar, base, and/or phosphate moiety as shown in FIG. 1 (Non-patent Document 4).

In these circumstances, the present inventors have successfully introduced two moieties each having a benzene or pyridine structure at the 3'-end of a nucleotide using an amidite reagent for introducing the benzene or pyridine structure carried on CPG resin, as described in Patent Document 1 (see, e.g., FIGS. 2 and 3). This technique has been developed in consideration of a key role of the 3'-dangling end in RNAi as described below, and can enhance nuclease resistance of an oligonucleotide without decreasing knockdown effect thereof.

More specifically, of RISC, which is known as a multi-domain protein involving in a process of degradation of a target mRNA by RNAi, the PAZ domain has recently been subjected to X-ray crystallography in the form of cocrystal with siRNA (J. B. Ma., K. Ye and D. J. Patel., Nature, 429, 318-322 (2004).) The result showed that the PAZ domain recognized the 3'-dangling end of the siRNA through two nucleotide molecules of the 3'-dangling end slipping in a hydrophobic pocket of the PAZ domain.
(J. J. Song., J. Liu., N. H. Tolia., J. Schneiderman., S. K. Smith., R. A. Martienssen., G. J. Hannon and L. Joshua-Tor., Nat. Struct. Biol., 10, 1026-1032 (2003), K. S. Yan., S. Yan., A. Farooq., A. Han., L. Zeng and M. M. Zhou., Nature., 426, 468-474 (2003), Zhang., F. A. Kolb., L. Jaskiewicz., E. Westhof and W. Filipowicz., Cell., 118, 57-68 (2003), and A. Lingel., B. Simon., E. Izaurralde and M. Sattler., Nature., 426, 465-469 (2003)). From this finding, the present inventors thought that an oligonucleotide can exhibit an enhanced knockdown effect by chemical modification with two hydrophobic groups each having a benzene or pyridine structure as substitutes for two nucleotide molecules of the 3'-dangling end, and have developed the oligonucleotide derivative described in Patent Document 1.

In association with the present invention, the present inventors have also successfully developed a technique for enhancing nuclease resistance and activity of silencing of an siRNA by converting a diester phosphate bond of the 3'-dangling end of the siRNA into a carbamate or urea bond, or the negatively charged bond into a bond with no charge, and thereby providing better permeability through a nuclear membrane (Non-patent Document 5).

REFERENCES

Patent Document

[Patent Document 1] WO2007/094135

Non-Patent Document

[Non-patent Document 1] L. Beigelman., J. A McSwiggen., K. G. Draper et al., J Biolchem 270, 25702-25708 (1995) 27
[Non-patent Document 2] S. P. Zinnen K. Domenico., M. Wilson et al., RNA 8, 214-228 (2002)
[Non-patent Document 3] S. Agrawaland E. R. Kandimalla., Curr. Cancer Drug Targets., 1, 197-209 (2001)
[Non-patent Document 4] H. Hoshi, FEBS Letters 521, 197-199 (2002)
[Non-patent Document 5] Y. Ueno, T. Naito, K. Kawada, A. Shibata, Hye-Sook Kim Y. Wataya, Y. Kidade, Biochem Biophys Res Commun 330, 1168-1175 (2005)

SUMMARY OF THE INVENTION

Problem to be Solved by the Invention

The synthesis of the oligonucleotide derivative chemically modified with two moieties each having a benzene or pyridine structure at the 3'-end in Patent Document 1, however, has a disadvantage of laborious preparation of a carrier used for the synthesis through many steps (see, e.g., FIGS. 2 and 3). The preparation of the carrier has another disadvantage of requirement of a highly skilled person and scrupulous attention in reacting a chemically unstable amidite with a hydroxymethyl group on a benzene or pyridine structure bonded to a carrier through a linker to make the series of reactions a success.

Considering these circumstances, the present inventors have accomplished the present invention. The present invention provides a modification carrier for synthesizing oligonucleotide derivative that enables to easily synthesize an oligonucleotide derivative chemically modified at the 3'-end with two moieties each having a benzene or pyridine structure with a few steps, and also provides an aromatic compound serving as a precursor for preparing the modification carrier.

The present invention also provides an oligonucleotide derivative and an oligonucleotide construct using the same, that is chemically modified at the 3'-end with two moieties each having a benzene or pyridine structure, and has good permeability through a cell membrane and excellent nuclease resistance.

Means for Solving the Problem

In preparation of the carrier used for synthesizing an oligonucleotide derivative chemically modified at the 3'-end with two units each having a benzene or pyridine structure described in Patent Document 1, aromatic rings were linked through a diester phosphate bond according to the same method using an amidite as in DNA and RNA synthesis. The preparation thus employed a chemically unstable amidite as an intermediate. This was responsible for increased steps for the synthesis and difficulty of the synthesis. As thus, the present inventors employed a urea bond for linking aromatic rings instead of a diester phosphate bond, because the linkage via a urea bond can be very easily and quantitatively formed by coupling aromatic rings with carbonyldiimidazole. A linkage of aromatic rings via a thiourea bond can also be very easily and quantitatively formed via a corresponding isothiocyanate using similar starting materials.

The modification carrier for synthesizing oligonucleotide derivative of the present invention is characterized by having a unit and a carrier carrying the unit directly or via a linker, the unit being represented by the formula (a):

[formula 1]

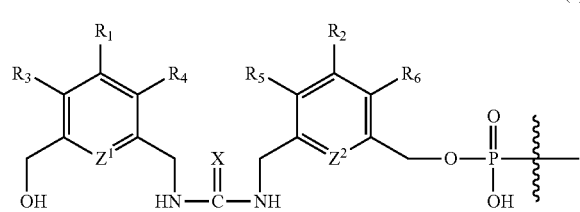

wherein, $R_1$ to $R_6$ each independently represent hydrogen or a substituent other than hydrogen; $Z^1$ and $Z^2$ each independently represent CH or nitrogen; and X represents oxygen or sulfur. Examples of the substituent other than hydrogen in $R_1$ to $R_6$ include an alkyl, an aryl, a haloalkyl, and a halogen groups.

In the modification carrier for synthesizing oligonucleotide derivative of the present invention, aromatic rings are linked via a urea or thiourea bond, and a hydroxymethyl group is bonded to the terminal aromatic ring. According to this structure, an oligonucleotide having any sequence can be linked with these aromatic rings through bonding of an amidite derivative of the nucleotide to the hydroxymethyl group, which strategy is frequently used in synthesis of DNA and RNA. The linkage of aromatic rings via a urea bond can be very easily and quantitatively formed by coupling aromatic rings with carbonyl diimidazole. The linkage of aromatic rings via a thiourea bond can also be very easily and quantitatively formed via a corresponding isothiocyanate using similar starting materials.

Any carrier can be used if it has a functionality that can bond to the unit represented by the formula (a) (formula 1) or a linker. Examples of the carrier include glasses such as microporous glass and porous glass, and plastics such as polyester, polyethylene, polypropylene, acrylonitrile butadiene styrene, nylon, acrylic, fluorine, polycarbonate, polyurethane, methylpentene, phenol, melamine, epoxy, and vinyl chloride resins. The carrier can have any form, including bead, plate (board), fiber, sphere, polygon, and powder.

Any linker can be used if it can chemically connect the unit represented by the formula (a) (formula 1) with the carrier. For example, common linkers used in automatic synthesis of DNA and RNA can be used. Specific examples of the linker include a succinate ester linker, an oxalate ester linker, a silanediyl linker, and a silyl linker, which are shown below.

[formula 2]

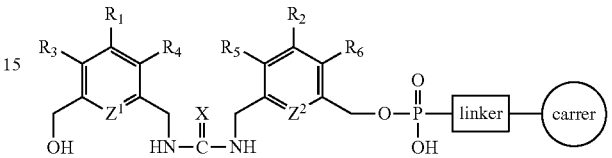

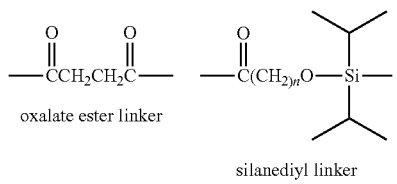

oxalate ester linker silanediyl linker

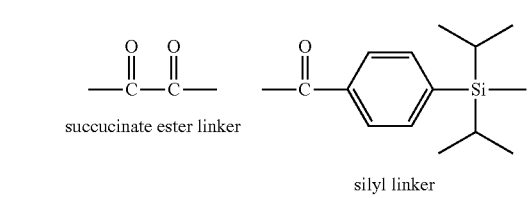

succucinate ester linker silyl linker

The modification carrier for synthesizing oligonucleotide derivative of the present invention can be easily produced from the aromatic compound precursor represented by the formula (A):

[formula 3]

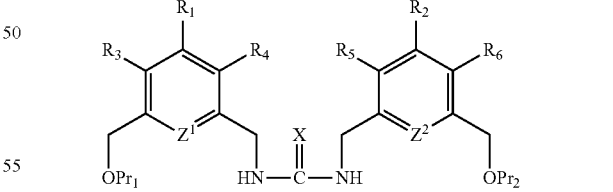

wherein, $R_1$ to $R_6$ each independently represent hydrogen or a substituent other than hydrogen; $Z^1$ and $Z^2$ each independently represent CH or nitrogen; X represents oxygen or sulfur; and $Pr_1$ and $Pr_2$ each independently represent a protecting group for a hydroxyl group.

In the modification carrier for synthesizing oligonucleotide derivative of the present invention, the unit represented by the formula ($a_1$) can also be carried on the carrier directly or via a linker:

[formula 4]

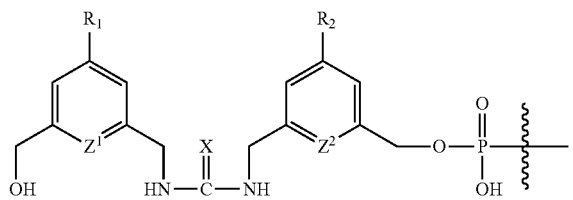

(a₁)

wherein, $R_1$ and $R_2$ each independently represent an alkyl, aryl, haloalkyl or halogen group; $Z^1$ and $Z^2$ each independently represent CH or nitrogen; and X represents oxygen or sulfur. $R_1$ and $R_2$ each particularly preferably represent an alkyl or haloalkyl group such as a fluoroalkyl group. The present inventors have confirmed that use of such a modification carrier for synthesizing oligonucleotide derivative enables to easily synthesize an oligonucleotide derivative at high yield with a few steps.

The modification carrier for synthesizing oligonucleotide derivative having the unit of formula (a₁) can be easily produced from an aromatic compound precursor represented by the formula (A₁):

[formula 5]

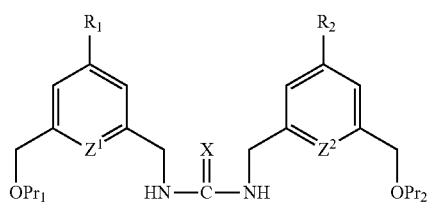

(A₁)

wherein, $R_1$ and $R_2$ each independently represent an alkyl, aryl, haloalkyl or halogen group; $Z^1$ and $Z^2$ each independently represent CH or nitrogen; X represents oxygen or sulfur; and $Pr_1$ and $Pr_2$ each independently represent a protecting group for a hydroxyl group. $R_1$ and $R_2$ each particularly preferably represent an alkyl or haloalkyl group such as a fluoroalkyl group.

In the modification carrier for synthesizing oligonucleotide derivative of the present invention, the unit represented by the formula (a₂) can also be carried on the carrier directly or via a linker:

[formula 6]

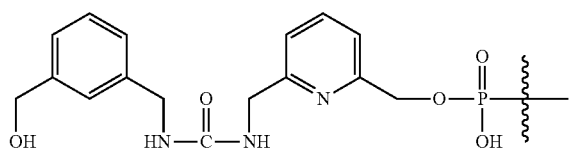

(a₂)

The present inventors have confirmed that use of such a modification carrier for synthesizing oligonucleotide derivative also enables to easily synthesize an oligonucleotide derivative at high yield with a few steps.

The modification carrier for synthesizing oligonucleotide derivative having the unit of formula (a₂) can be easily produced from an aromatic compound precursor represented by the formula (A₂):

[formula 7]

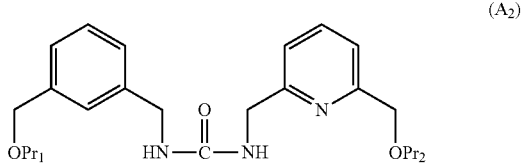

(A₂)

The oligonucleotide derivative of the present invention is characterized by being modified at the 3'-end thereof with a unit represented by the formula (a):

[formula 8]

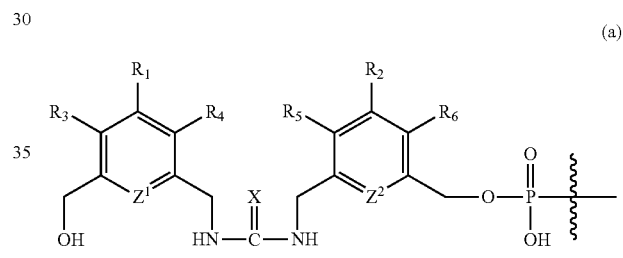

(a)

wherein, $R_1$ to $R_6$ each independently represent hydrogen or a substituent other than hydrogen; $Z^1$ and $Z^2$ each independently represent CH or nitrogen; and X represents oxygen or sulfur.

The oligonucleotide derivative of the present invention can be easily synthesized using the modification carrier for synthesizing oligonucleotide derivative of the present invention as one of starting materials according to a method for synthesizing an oligonucleotide that has been conventionally used in synthesis of DNA and RNA. The oligonucleotide derivative has two aromatic rings at the 3'-end, which aromatic rings are linked via a urea or thiourea bond. This structure makes the 3'-end moiety hydrophobic, and thereby providing good permeability through a cell membrane and excellent nuclease resistance to the oligonucleotide derivative. As thus, the oligonucleotide derivative of the present invention can exhibit its effect for a longer time in a cell. In addition, when used in RNAi, the oligonucleotide derivative of the present invention easily slips the 3'-end moiety into a hydrophobic pocket of the PAZ domain in RISC, and will enhance an effect of knockdown.

In the oligonucleotide derivative of the present invention, the unit represented by the formula (a₁) can also modify the 3'-end of the oligonucleotide:

[formula 9]

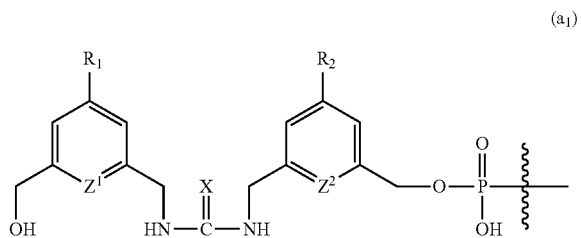

(a₁)

wherein, $R_1$ and $R_2$ each independently represent an alkyl, aryl, haloalkyl or halogen group; $Z^1$ and $Z^2$ each independently represent CH or nitrogen; X represents oxygen or sulfur; and $Pr_1$ and $Pr_2$ each independently represent a protecting group for a hydroxyl group. $R_1$ and $R_2$ each particularly preferably represent an alkyl or haloalkyl group such as a fluoroalkyl group. The present inventors have confirmed that such an oligonucleotide derivative has excellent nuclease resistance and can exhibit an effect of knockdown in RNAi for a longer time in a cell.

In the oligonucleotide derivative of the present invention, the unit represented by the formula (a₂) can also modify the 3'-end of the oligonucleotide:

[formula 10]

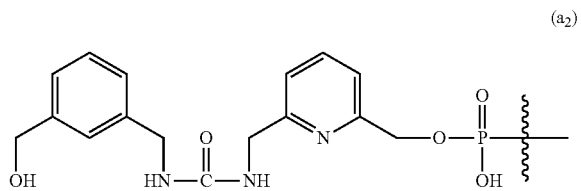

(a₂)

The present inventors have confirmed that such an oligonucleotide derivative has excellent nuclease resistance and can exhibit an effect of knockdown in RNAi for a longer time in a cell.

The oligonucleotide derivative of the present invention can have an oligonucleotide sequence corresponding to a partial mRNA sequence of a target gene or the complementary sequence thereof. A length of the oligonucleotide can be not less than 10- to not more than 35-mer. The oligonucleotide may be an oligoribonucleotide.

The oligonucleotide construct of the present invention is for regulating gene expression, and is characterized by comprising any one of oligonucleotide derivatives described above. The oligonucleotide construct can be of any class selected from single- and double-strand DNAs, single- and double-strand RNAs, DNA/RNA chimeras, and DNA/RNA hybrids. In terms of function, it can be of any type selected from antigene, antisense, aptamer, siRNA, miRNA, shRNA, and ribozyme.

According to the present invention, the oligonucleotide construct comprising any one of oligonucleotide derivatives described above can be used in gene diagnosis. The oligonucleotide construct can also be used as a probe or primer.

MODES FOR CARRYING OUT THE INVENTION (Modification Carrier for Synthesizing Oligonucleotide Derivative)

The modification carrier for synthesizing oligonucleotide derivative of the present invention can be prepared as described below. As used herein, the "nucleotide" refers nucleotide that may be modified.

(Oligonucleotide Derivative)

The oligonucleotide derivative of the present invention can be produced by various methods for nucleic acid synthesis including an amidite method using the modification carrier for synthesizing oligonucleotide derivative of the present invention. For protecting a hydroxyl group, various known hydroxyl-protecting groups can be used without specific limitation. Specific examples of the protecting group include a benzyl, an acetyl, and a benzoyl groups. Particularly preferred is a benzyl group. Examples of an amino-protecting group include a phthalate and a benzoyl groups. Particularly preferred is a phthalate group.

An antigene, an antisense, an aptamer, an miRNA, and a ribozyme constructed with the oligonucleotide derivative of the present invention are characterized only by comprising a unit represented by the formula (a). In the case of a fixed probe on a solid carrier, the probe can be produced such that it comprises a unit represented by the formula (a) at the free-end portion. In the case of a primer, it may comprise a unit represented by the formula (a) at an appropriate site according to need.

As used herein, the "oligonucleotide" refers to a polymer made of nucleotides as a monomer unit, that generally make up oligonucleotides and polynucleotides. The "oligonucleotide" more particularly refers to a polymer made of deoxyribonucleotides and/or ribonucleotides as a monomer unit. In general, of nucleotide polymers, a polymer made of deoxyribonucleotides as a monomer unit is referred to as DNA, and a polymer made of ribonucleotides as a monomer unit is referred to as RNA. The oligonucleotide derivative of the present invention includes oligomers of these monomer units, as well as so-called DNA and RNA. The oligonucleotide also includes RNA/DNA chimeras. The "oligonucleotide that may be modified" includes not only oligonucleotides made of only nucleotides having a naturally-occurring base including guanine, cytosine, thymine, adenine, uracil, and methylcytosine, which are purines and pyrimidines, but also oligonucleotides made of nucleotides one or more of which are chemically modified at any moiety of base, sugar, and phosphate.

The oligonucleotide derivative of the present invention can have a partial sequence of the sense or antisense strand of DNA or mRNA of a target gene or a complementary sequence thereof. Such a complementarity of the oligonucleotide derivative enables it to hybridize to a target nucleic acid of any kind to effect an intended function of the oligonucleotide derivative. In the oligonucleotide derivative of the present invention, a length of the oligonucleotide is not specifically limited and can be defined according to an application. Considering with ease of synthesis and achievement of expected effects of an oligonucleotide, the length is preferably not less than 10- to not more than 35-mer. In cases of antisense, the length is around the range from not less than 10- to not more than 30-mer. In cases of siRNA, a total length of A and B chains is preferably not less than 15- to not more than 35-mer, and more preferably not more than 30-mer. In cases of primer, the length is preferably not less than 10- to not more than 30-mer. In cases of probe, the length is preferably not less than 10- to not more than 30-mer.

In case of using the oligonucleotide derivative of the present invention in, for example, an siRNA, an shRNA, an antisense, a ribozyme, and an aptamer, the oligonucleotide derivative may be an oligoribonucleotide comprising a monomer unit that may be modified.

(Oligonucleotide Construct)

The oligonucleotide construct of the present invention comprises the oligonucleotide derivative of the present invention. According to a type of the oligonucleotide derivative, the oligonucleotide construct may have a single form of single-strand DNA, double-strand DNA, single-strand RNA, double-strand RNA, DNA/RNA chimera, DNA/RNA hybrid, or the like, or a combined form thereof. The oligonucleotide construct may comprise a modified oligonucleotide, because, as described above, an oligonucleotide moiety of the oligonucleotide derivative includes a modified oligonucleotide.

The oligonucleotide construct of the present invention has enhanced nuclease resistance, and thus can be effective in various applications for regulating gene expression and for research or diagnosis. Examples of the application for regulating gene expression include antigene, antisense, aptamer, siRNA, miRNA, siRNA, and ribozyme. Particularly in cases of siRNA and siRNA, the oligonucleotide construct can have enhanced both nuclease resistance and gene silencing activity by having a unit represented by the formula (a) introduced at dT in a 3'-overhang end.

Examples of the application for diagnosis or research include probe and primer. A probe is an oligonucleotide, that has a defined sequence specific to a target nucleic acid as designed or selected and hybridizes to the target under a given stringency condition. A probe constructed with the oligonucleotide derivative of the present invention has enhanced nuclease resistance, and thus can be less affected from or can avoid effects of nucleases contained in a sample comprising a target nucleic acid. Accordingly, a sample can be prepared with low degree of removal of nucleases or even without a removal treatment of nucleases, resulting in simple and easy genetic diagnosis and test. In hybridization of such a probe with a target, the probe can be fixed on an appropriate solid carrier such as a glass plate, a plastic plate, and beads. The present invention also includes a solid carrier on which a probe constructed with the oligonucleotide derivative of the present invention is fixed.

(Use of Oligonucleotide Derivative)

The oligonucleotide derivative of the present invention can be used in constructs so as to function like as an siRNA or antisense to be used as a gene-silencing agent. The oligonucleotide derivative can also be used as an active constituent of a pharmaceutical composition for preventing or treating a disease in human or other animals. For example, the oligonucleotide derivative of the present invention constructed as a gene silencing agent is effective for preventing or treating a disease accompanying with a gene expression.

The oligonucleotide derivative of the present invention can also be used in constructs so as to perform its function of hybridizing to be used as a test or diagnostic reagent such as a probe or a primer. The oligonucleotide construct can further be supported on a solid carrier such as chip and bead to be used as a testing or diagnostic device or a part thereof. Such a test or diagnostic reagent can be used together with other reagent, diagnostic agent, or device as a test or diagnostic kit.

The oligonucleotide derivative of the present invention can also be used in a method for gene silencing, which uses the effects of the oligonucleotide construct comprising the oligonucleotide derivative of the present invention to suppress a gene expression, and in a method for detecting a gene, which uses the function of the oligonucleotide construct to hybridize.

EXAMPLES

Examples will be described in detail below for illustrating the present invention.

In Examples, instruments used are as follows.

| | (Instrument) |
|---|---|
| NMR spectrum | JEOL JNM-α400 |
| GC/MS | SHIMADZU GCMS-QP 2010A |
| absorption spectrometer | HITACHI U-2001 spectrophotometer, GE Healthcare Nano Vue |
| DNA/RNA synthesizer | Applied Biosystems Model 3400 |
| Tm measuring instrument | SHIMADZU UV 2400 |
| HPLC | SPD-10AVP, SCL-10AVP, LC-10AVP, DGU-10A, CTO-10AVP, C-R8A |
| MALDI-TOF/MS | SHIMADZU AXIMA-CFR plus plate luminometer ATTO Luminescenser JNRII |

In the description of Examples herein, the following abbreviations are also used. (Abbreviation)

| | |
|---|---|
| APS | ammonium peroxodisulfate |
| CPG | controlled pore glass |
| DMAP | 4-dimethylaminopyridine |
| DMTrCl | 4.4'-dimethoxytritylchloride |
| EDC | 1-ethyl-3-(3-dimethylaminopropyl) carbodiimide |
| EDTA | ethylenediamine-N,N,N',N'-tetraacetic acid |
| MALDI-TOF | matrix assisted laser desorption ionization - time of flight |
| PAGE | polyacrylamide gel electrophoresis |
| TBAF | tetrabutylammonium fluoride |
| TBE | tris-borate-EDTA |
| TEAA | triethylammonium acetate |
| TEMED | N,N,N',N'-tetramethylethylenediamine |
| Tm | melting temperature |
| Tris | tris(hydroxymethyl) aminomethane |

Example 1

<Production of a Modification Carrier for Synthesizing Oligonucleotide Derivative Having a Benzene Ring and a Pyridine Ring Linked Via a Urea Bond>

In Example 1, a modification carrier for synthesizing oligonucleotide derivative having a benzene-pyridine structure as a primary moiety was produced as follows.

2,6-pyridinedimethanol as a starting material was reacted with tert-butyldimethylsilyl chloride (TBDMSCl) in the presence of sodium hydride to give a silyl compound 1 protected with a TBDMS group at one of two hydroxyl groups with 49% yield. The silyl compound 1 was brominated and azidated by a one-pot synthesis using carbon tetrabromide and sodium azide together to give an azide compound 2 with 76% yield. The azide compound 2 was subjected to a selective reduction of azide with hydrogen in the presence of a 5% palladium-ethylenediamine complex as a catalyst to give a pyridine derivative 3 with 80% yield.

Besides this, as shown in the following scheme, 3-cyannobenzyl alcohol as a starting material was reacted with 4,4'-dimethoxytrityl chloride (DMTrCl) to give a dimethoxytrityl compound 4 with 91% yield. The compound 4 was reduced at a cyano group with lithium aluminum hydride to give a benzylamino compound 5 with 69% yield. The benzylamino compound 5 was coupled with the pyridine derivative 3 prepared above using carbonyl diimidazole to give a urea derivative 6 with 43% yield. It is noted that a thiourea derivative can also be easily and quantitatively produced through a corresponding isothiocyanate intermediate from corresponding starting materials. The thiourea derivative can be used to produce a modification carrier for synthesizing oligonucleotide derivative having a thiourea bond in the same way as to produce a modification carrier for synthesizing oligonucleotide derivative having a urea bond, shown below.

The urea derivative 6 prepared as above was treated with TBAF to give a desilylated compound 7 shown below with 98% yield. The compound 7 was succinylated with succinic anhydride according to a standard method, and reacted with a CPG resin in the presence of a dehydration-condensation agent to give a modification carrier for synthesizing oligonucleotide derivative 9 of Example 1 with an activity of 38.5 μmol/g.

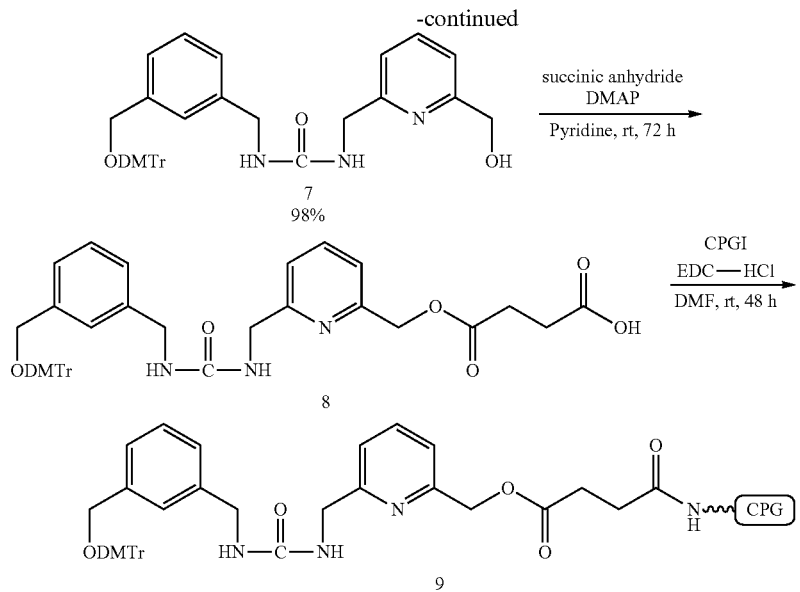

The process of producing the modification carrier for synthesizing oligonucleotide derivative (9) will be described in more detail below.

Preparation of 2-[(tert-butyldimethylsilyloxy)methyl]-6-hydroxymethylpyridine (1)

To a solution of 60% NaH (1.45 g, 35.9 mmol) in DMF (60 mL), which was stirred and cooled with ice, was added a solution of 2,6-pyridinedimethanol (5.00 g, 35.9 mmol) in DMF (30 mL), and stirred for 1 hour at a room temperature under Ar atmosphere. To the mixture was added a solution of tert-butyldimethylchlorosilane (6.54 g, 43.3 mmol) in DMF (40 mL), and stirred for additional 12 hours. TLC was used to confirm there was no starting material in the reaction mixture. Then, the mixture was subjected to extraction with EtOAc and 10% NaHCO$_3$ aq. The organic layer was washed with sat. NaClaq., dried over anhydrous Na$_2$SO$_4$, and evaporated under reduced pressure to remove the solvent. The residue was purified by silica gel column chromatography (Hex:EtOAc=5:1) to give 2-[(tert-butyldimethylsilyloxy)methyl]-6-hydroxymethylpyridine (1) (4.46 g, 49%) as a colorless oil.

$^1$H-NMR (CDCl$_3$, 400 MHz)

δ=7.66 (1H, d, J=7.6 Hz, Ar—H), 7.39 (1H, d, J=7.6 Hz, Ar—H), 7.10 (1H, d, J=7.6 Hz, Ar—H), 4.80 (2H, s, CH$_2$O), 4.71 (2H, s, CH$_2$O), 0.95 (9H, s, t-C$_4$H$_9$Si), 0.11 (6H, s, (CH$_3$)$_2$Si)

$^{13}$C-NMR (CDCl$_3$, 100 MHz)

δ=160.3, 157.9, 157.9, 137.3, 118.5, 65.8, 63.9, 25.9, 18.3, −5.4

Preparation of 2-azidomethyl-6-[(tert-butyldimethylsilyloxy)methyl]pyridine (2)

A mixture of 2-[(tert-butyldimethylsilyloxy)methyl]-6-hydroxymethylpyridine (1) (2.14 g, 8.42 mmol), sodium azide (2.73 g, 42.0 mmol), triphenylphosphine (2.65 g, 10.10 mmol), and carbon tetrabromide (3.07 g, 9.29 mmol) was dried in vacuo, and dissolved in DMF (64 mL). To the solution was added triethylamine (2.64 mL) and stirred for 25 hours under Ar atmosphere. TLC was used to confirm there was no starting material in the reaction mixture. Then, the mixture was subjected to extraction with EtOAc and water. The organic layer was washed with sat. NaCl aq., dried over anhydrous Na$_2$SO$_4$, and evaporated under reduced pressure to remove the solvent. The residue was purified by silica gel column chromatography (Hex:EtOAc=50:1) to give 2-azidomethyl-6-[(tert-butyldimethylsilyloxy)methyl]pyridine (2) (1.77 g, 76%) as a pale-yellow oil.

$^1$H-NMR (CDCl$_3$, 400 MHz)

δ=7.73 (1H, t, J=7.6 Hz, Ar—H), 7.47 (1H, d, J=7.6 Hz, Ar—H), 7.20 (1H, d, J=7.6 Hz, Ar—H), 4.83 (2H, s, CH$_2$O), 4.44 (2H, s, CH$_2$O), 0.96 (9H, s, t-C$_4$H$_9$Si), 0.12 (6H, s, (CH$_3$)$_2$Si)

$^{13}$C-NMR (CDCl$_3$, 100 MHz)

δ=161.6, 154.4, 137.6, 120.0, 119.2, 65.9, 55.6, 25.9, 18.3, −5.4

Preparation of 2-aminomethyl-6-[(tert-butyldimethylsilyloxy)methyl]pyridine (3)

A suspension of 2-azidomethyl-6-[(tert-butyldimethylsilyloxy)methyl]pyridine (2) (0.83 g, 2.98 mmol) and 5% Pd/C (en) (83.0 mg, 10 wt %) in MeOH (20 mL) was vigorously stirred for 5 hours at a room temperature under a hydrogen atmosphere. TLC was used to confirm there was no starting material in the reaction mixture. Then, the catalyst was removed by suction filtration with a kiriyama funnel. The filtrate was evaporated under reduced pressure. The residue was purified by silica gel column chromatography (CHCl$_3$:MeOH=30:1 to 10:1) to give 2-aminomethyl-6-[(tert-butyldimethylsilyloxy)methyl]pyridine (3) (603 mg, 80%) as a yellow oil.

$^1$H-NMR (CDCl$_3$, 400 MHz)

δ=7.66 (1H, t, J=7.8 Hz, Ar—H), 7.37 (1H, d, J=7.8 Hz, Ar—H), 7.13 (1H, d, J=7.6 Hz, Ar—H), 4.82 (2H, s, CH$_2$O), 3.94 (2H, s, CH$_2$N), 0.96 (9H, s, t-C$_4$H$_9$Si), 0.12 (6H, s, (CH$_3$)$_2$Si)

$^{13}$C-NMR (CDCl$_3$, 100 MHz)

δ=160.8, 160.7, 136.9, 119.0, 117.8, 65.9, 47.6, 25.7, 18.2, −5.4

Preparation of 3-(4,4'-dimethoxytrityloxymethyl)benzonitrile (4)

In DMF (23 mL) and pyridine (23 mL), suspended were 3-hydroxymethylbenzonitrile (1.12 g, 8.38 mmol) and 4,4'-dimethoxytritylchloride (3.41 g, 10.06 mmol). The suspension was stirred for 12 hours at a room temperature under Ar atmosphere. TLC was used to confirm there was no starting material in the reaction mixture. Then, to the suspension was added iced water (20 mL). The mixture was subjected to extraction with EtOAc and water. The organic layer was washed with sat. NaCl aq., dried over anhydrous $Na_2SO_4$, and evaporated under reduced pressure to remove the solvent. The residue was purified by silica gel column chromatography (Hex:EtOAc=10:1) to give 3-(4,4'-dimethoxytrityloxymethyl)benzonitrile (4) (3.31 mg, 91%) as a colorless oil.

$^1$H-NMR (CDCl$_3$, 400 MHz)

δ=7.23-7.68 (17H, m, Ar—H), 6.84 (4H, d, J=8.8 Hz, Ar—H), 4.21 (2H, s, CH$_2$O), 3.79 (6H, s, CH$_3$O)

$^{13}$C-NMR (CDCl$_3$, 100 MHz)

δ=158.3, 144.4, 135.4, 130.5, 130.4, 129.5, 128.9, 128.5, 126.9, 118.6, 113.7, 112.1, 111.9, 111.8, 86.4, 56.9, 55.5, 54.0

Preparation of 3-(4,4'-dimethoxytrityloxymethyl)benzylamine (5)

To a suspension of LiAlH$_4$ (238 mg, 6.28 mmol) in diethyl ether (30 mL), which was stirred and cooled with ice, was added dropwise a solution of 3-(4,4'-dimethoxytrityloxymethyl)benzonitrile (4) (0.86 g, 1.98 mmol) in diethyl ether (90 mL). The mixture was stirred for 16 hours at a room temperature under Ar atmosphere. TLC was used to confirm there was no starting material in the reaction mixture. Then, to the mixture were added water (1.2 mL) and MeOH (7.2 mL) and stirred for additional 30 minutes. Then, a formed salt was removed by suction filtration. The filtrate was evaporated under reduced pressure. The residue was purified by silica gel column chromatography (CHCl$_3$:MeOH=100:1) to give 3-(4,4'-dimethoxytrityloxymethyl)benzylamine (5) (0.58 g, 69%) as a colorless oil.

$^1$H-NMR (CDCl$_3$, 400 MHz)

δ=7.21-7.52 (17H, m, Ar—H), 6.83 (4H, d, J=8.8 Hz, Ar—H), 4.16 (2H, s, CH$_2$O), 3.86 (2H, s, CH$_2$N), 3.79 (6H, s, CH$_3$O)

$^{13}$C-NMR (CDCl$_3$, 100 MHz)

δ=158.4, 145.0, 143.2, 139.6, 136.2, 130.0, 128.4, 128.2, 127.8, 126.7, 125.7, 125.6, 125.4, 113.1, 86.3, 65.5, 55.1, 46.5

Preparation of N-[3-(4,4'-dimethoxytrityloxymethyl)benzyl]-N'-{[6-(tert-butyldimethylsilyloxy)methylpyridin-2-yl]methyl}urea (6)

A suspension of 3-(4,4'-dimethoxytrityloxymethyl)benzylamine (5) (455 mg, 1.04 mmol) and 1,1'-carbonyldiimidazole (170 mg, 1.05 mmol) in THF (52 mL) was stirred for 24 hours at a room temperature under Ar atmosphere. TLC was used to confirm there was no starting material in the reaction mixture. Then, to the suspension was added dropwise a solution of 2-aminomethyl-6-[(tert-butyldimethylsilyloxy)methyl]pyridine (3) (593 mg, 2.35 mmol) in THF (13 mL), and further stirred for 48 hours. The reaction mixture was evaporated under reduced pressure. The residue was purified by silica gel column chromatography (CHCl$_3$:MeOH=100:1) to give N-[3-(4,4'-dimethoxytrityloxymethyl)benzyl]-N'-{[6-(tert-butyldimethylsilyloxy)methylpyridin-2-yl]methyl}urea (6) (406 mg, 54%) as a colorless oil.

$^1$H-NMR (CDCl$_3$, 400 MHz)

δ=7.61-7.07 (16H, m, Ar—H), 6.82-6.80 (4H, d, J=8.8 Hz, Ar—H), 4.71 (2H, s, CH$_2$), 4.43 (2H, s, CH$_2$), 4.37 (2H, s, CH$_2$), 4.16 (2H, s, CH$_2$), 3.78 (6H, s, CH$_3$O), 0.95 (9H, s, t-C$_4$H$_9$Si), 0.10 (6H, s, (CH$_3$)$_2$Si)

$^{13}$C-NMR (CDCl$_3$, 100 MHz)

δ=160.6, 158.4, 158.2, 156.4, 145.0, 139.7, 139.1, 137.4, 136.2, 130.0, 128.5, 128.1, 127.8, 126.7, 126.2, 126.0, 125.9, 120.0, 118.3, 113.1, 86.4, 65.8, 65.4, 55.2, 45.6, 44.5, 25.9, 18.3, −5.4

Mass (EI) m/z: 717 (M$^+$)

Preparation of N-[3-(4,4'-dimethoxytrityloxymethyl)benzyl]-N'-[(6-hydroxymethylpyridin-2-yl)methyl]urea (7)

To a suspension of N-[3-(4,4'-dimethoxytrityloxymethyl)benzyl]-N'-{[6-(tert-butyldimethylsilyloxy)methylpyridin-2-yl]methyl}urea (6) (410 mg, 0.57 mmol) in THF (2.2 mL), which was stirred, was added dropwise a solution of 1.0M TBAF in THF (0.64 mL), and stirred for 4 hours at a room temperature under Ar atmosphere. TLC was used to confirm there was no starting material in the reaction mixture. Then, the reaction mixture was evaporated under reduced pressure. The residue was purified by silica gel column chromatography (CHCl$_3$:MeOH=20:1) to give N-[3-(4,4'-dimethoxytrityloxymethyl)benzyl]-N'-[(6-hydroxymethylpyridin-2-yl)methyl]urea (7) (336 mg, 98%) as colorless crystals.

$^1$H-NMR (CDCl$_3$, 400 MHz)

δ=7.52-7.02 (16H, m, Ar—H), 6.82-6.80 (4H, d, J=8.8 Hz, Ar—H), 4.59 (2H, s, CH$_2$), 4.39 (2H, s, CH$_2$), 4.29 (2H, s, CH$_2$), 4.13 (2H, s, CH$_2$), 3.76 (6H, s, CH$_3$O)

$^{13}$C-NMR (CDCl$_3$, 100 MHz)

δ=158.6, 158.4, 157.1, 144.9, 139.5, 139.2, 137.3, 136.1, 130.0, 128.5, 128.1, 127.8, 126.7, 126.0, 125.8, 125.7, 120.2, 118.9, 113.1, 86.4, 65.4, 64.1, 55.1, 45.3, 44.2

Preparation of the Modification Carrier for Synthesizing Oligonucleotide Derivative (9)

To a solution of N-[3-(4,4'-dimethoxytrityloxymethyl)benzyl]-N'-[(6-hydroxymethylpyridin-2-yl)methyl]urea (7) (290 mg, 0.47 mmol) in pyridine (4.7 mL) was added DMAP (1.24 mg, 1.42 mmol) and stirred for 72 hours at a room temperature under Ar atmosphere. TLC was used to confirm there was no starting material in the reaction mixture. Then, the reaction mixture was subjected to extraction with EtOAc and sat. NaHCO$_3$ aq. The organic layer was washed with sat. NaCl aq., dried over anhydrous Na$_2$SO$_4$, and evaporated under reduced pressure to give a succinyl compound (8). The succinyl compound (8) was dried in vacuo overnight, and dissolved in DMF (12 mL, 0.01M relative to CPG). The solution was well mixed with a CPG resin (120 μmol/g) (979 mg, 0.118 mmol). Then, to the mixture was added EDC.HCl (90 mg, 0.47 mmol) and shaken for 48 hours at a room temperature. The reaction mixture was washed with pyridine. Then, to the reaction mixture was added a solution of 0.1 M DMAP (pyridine:Ac$_2$O=9:1) (15 mL), and further shaken for 12 hours at a room temperature. The reaction mixture was washed with pyridine, EtOH, and MeCN and dried for 12 hours in vacuo to give a resin. The resin was measured about its activity. The activity was determined by placing 6 mg of dried CPG resin on a glass filter, filtering a solution of HClO$_4$:EtOH=3:2 through the filter, measuring an absorbance of the filtrate at UV 498 nm (wavelength of DMTr group), and substituting the value in the following equation. The measurement result showed an activity of 38.5 μmol/g.

$$\frac{\text{Abs. (498 nm)} \times \textit{Vol.} \text{ (solution) (mL)} \times 14.3}{\text{Weight (support) (mg)}} = \text{Activity} \quad \text{[equation 1]}$$

Comparative Example 1

Based on a procedure described in Patent Document 1, which had been developed by the present inventors, a modification carrier for synthesizing oligonucleotide derivative (19) of Comparative Example 1 was prepared according to the synthetic route of formula 14 The detail will be described below.

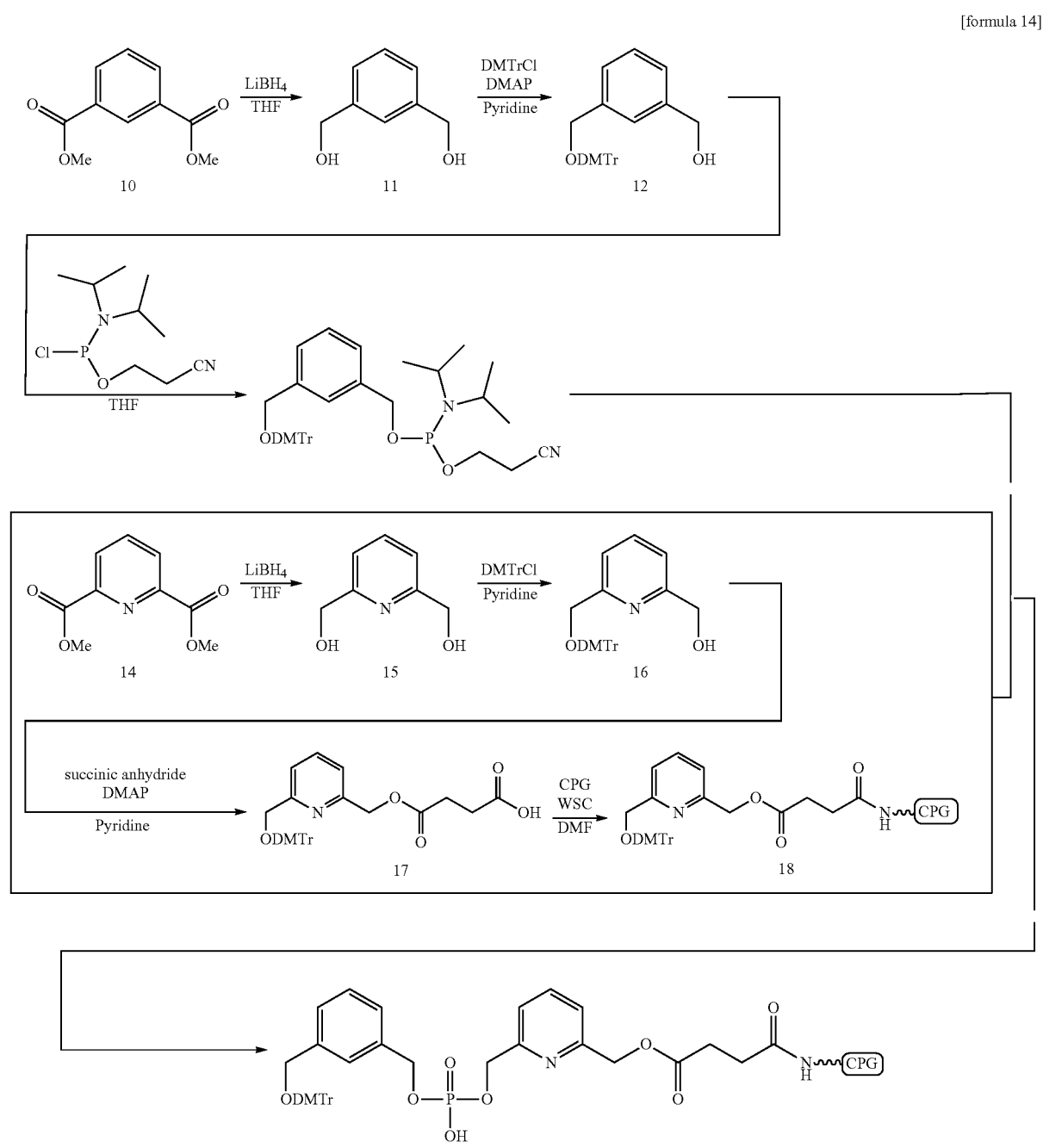

[formula 14]

Preparation Example of compound 11: 1,3-bis-hydroxymethylbenzene

Under Ar atmosphere, to dimethyl isophthalate (2.00 g, 10.30 mmol) were added dry THF (51.5 mL, 0.2M solution) and lithium borohydride (1.12 g, 51.5 mmol, 5 eq.), and stirred for 23 hours. Then, in an ice bath, to the mixture was added a few drops of acetic acid to neutralize the mixture, thereby quenching the reaction. The mixture was stirred for a while. Formed crystals were dissolved by adding MeOH. Although there was one spot of product as checked by TLC (Hex:EtOAc=1:1) during the reaction, after the reaction quenched, there were two spots of products on TLC. The solvent was distilled off under reduced pressure. Products were separated by silica gel column chromatography (only EtOAc) to give a compound (11) (1.36 g, 9.82 mmol, 95%).

$^1$H NMR (400 MHz, CDCl$_3$) δ [ppm]: 7.39-7.26 (4H, m, aromatic protons), 4.71 (4H, s, —CH$_2$—O—), 1.70 (2H, d, J=76.8 Hz, OH)

$^{13}$C NMR (100 MHz, CDCl$_3$) δ [ppm]: 139.28, 129.62, 128.47, 63.90

Mass (EI) m/z: 138 (M$^+$), 120, 107, 79, 65, 51.

HRMS (EI) Calcd for C$_8$H$_{10}$O$_2$ 138.06808 Found 138.06765.

Anal. Calcd for C$_8$H$_{10}$O$_2$: C, 69.54; H, 7.30. Found: C, 69.45; H, 7.23.

Preparation Example of compound 12: 1-(4,4'-dimethoxytrityloxy)methyl-3-hydroxymethylbenzene)

The compound (11) (0.5 g, 3.62 mmol) was dried in vacuo, and then dissolved in pyridine (18 mL). To the solution were added DMAP (22.1 mg, 0.18 mmol, 0.05 eq.) and 4,4'-dimethoxytrityl chloride (1.23 g, 3.62 mmol, 1 eq.), and stirred for 17 hours under Ar atmosphere. TLC (Hex:EtOAc=3:1) was used to confirm there was no starting material in the reaction mixture. The reaction mixture was subjected to extraction with EtOAc and sat. NaHCO$_3$ aq. The organic layer was washed with sat. NaCl aq., dried over anhydrous Na$_2$SO$_4$, and evaporated under reduced pressure to remove the solvent. Products were separated by silica gel column chromatography (Hex:EtOAc=4:1) to give a compound (12) (0.82 g, 1.86 mmol, 51%).

$^1$H NMR (400 MHz, CDCl$_3$) δ [ppm]: 7.52-6.82 (17H, m, DMTr and aromatic protons), 4.70 and 4.18 (4H, s, —CH$_2$—O—), 3.80 (6H, t, J=4.0 Hz, H-methoxy), 1.62 (2H, s, OH)

$^{13}$C NMR (100 MHz, CDCl$_3$) δ [ppm]: 158.42, 145.00, 140.76, 139.68, 136.24, 130.06, 128.50, 128.16, 127.83, 126.73, 126.31, 125.71, 125.55, 113.10, 86.39, 65.43, 55.20

Mass (EI) m/z: 440 (M$^+$), 303, 273, 227, 138, 121, 107, 79, 45.

HRMS (EI) Calcd for C$_{29}$H$_{28}$O$_4$ 440.19876 Found 440.19806. Anal. Calcd for C$_{29}$H$_{28}$O$_4$·⅕H$_2$O: C, 78.27; H, 6.45. Found: C, 78.33; H, 6.59.

Preparation Example of compound 13: 1-(4,4'-dimethoxytrityloxy)methyl-3-O-[(2-cyanoethyl)-(N,N-diisopropyl)]-phosphoamidicmethyl-hydroxymethylbenzene)

The compound (12) (0.35 g, 0.80 mmol) was dried in vacuo, and then dissolved in dry THF (8 mL). To the solution were added DIPEA (0.4 mL, 4.00 mmol, 5 eq.) and a phosphitylating agent (0.29 mL, 1.60 mmol, 2 eq.), and stirred for 1.5 hours under Ar atmosphere. TLC (only EtOAc) was used to confirm there was no starting material in the reaction mixture. The reaction mixture was subjected to extraction with EtOAc and sat. NaHCO$_3$ aq. The organic layer was washed with sat. NaCl aq., dried over anhydrous Na$_2$SO$_4$, and evaporated under reduced pressure to remove the solvent. Products were separated by neutral silica gel column chromatography (Hex:EtOAc=1:1) to give a compound (13) (0.48 g, 0.75 mmol, 94%).

$^{32}$P NMR (162 MHz, CDCl$_3$) δ [ppm]: 148.8

Mass (FAB) m/z: 641 ([M$^+$+H]), 303, 201, 154.

HRMS (FAB) Calcd for C$_{38}$H$_{46}$N$_2$O$_5$P 641.31443 Found 641.31292.

Preparation Example of Compound 15: 2,6-bis-hydroxymethylpyridine)

Under Ar atmosphere, to dimethyl 2,6-pyridinedicarboxylate (14) (2.00 g, 10.25 mmol) were added dry THF (51.3 mL, 0.2M solution) and lithium borohydride (1.16 g, 51.3 mmol, 5 eq.), and stirred for 16 hours. Then, in an ice bath, to the mixture was added a few drops of acetic acid to neutralize the reaction, thereby quenching the reaction. The mixture was stirred for awhile. Formed crystals were dissolved by adding methanol. Although there was one spot of product as checked by TLC (CHCl$_3$:MeOH=3:1) during the reaction, after the reaction quenched, there were two spots of products on TLC. The solvent was distilled off under reduced pressure. Products were separated by silica gel column chromatography (CHCl$_3$:MeOH=10:1 to 3:1) to give a compound (15) (0.40 g, 2.88 mmol, 28%).

$^1$H NMR (400 MHz, CDCl$_3$) δ [ppm]: 7.72-7.00 (3H, m, aromatic protons), 4.79 (4H, s, —CH$_2$—)

$^{13}$C NMR (100 MHz, CDCl$_3$) δ [ppm]: 158.37, 137.44, 119.12, 64.33

Mass (FAB) m/z: 140 ([M$^+$+H]), 277, 185, 93, 57.

HRMS (FAB) Calcd for C$_7$H$_{10}$NO$_2$ 140.07115 Found 140.07054.

Anal. Calcd for C$_7$H$_{10}$NO$_2$:
C, 60.42; H, 6.52; N, 10.07. Found: C, 60.28; H, 6.50; N, 9.95.

Preparation Example of Compound 16: 2-(4,4'-dimethoxytrityloxy)methyl-6-hydroxymethylpyridine The compound (15) (0.5 g, 3.60 mmol) was dried in vacuo, and then dissolved in pyridine (18 mL). To the solution were added DMAP (22.1 mg, 0.18 mmol, 0.05 eq.) and 4,4'-dimethoxytrityl chloride (1.22 g, 3.60 mmol, 1 eq.), and stirred for 16 hours under Ar atmosphere. TLC (Hex:EtOAc=1:1) was used to confirm there was no starting material in the reaction mixture. The reaction mixture was subjected to extraction with EtOAc and sat. NaHCO$_3$ aq. The organic layer was washed with sat. NaCl aq., dried over anhydrous Na$_2$SO$_4$, and evaporated under reduced pressure to remove the solvent. Products were separated by silica gel column chromatography (Hex:EtOAc=4:1 to 3:1) to give a compound (16) (0.27 g, 0.61 mmol, 43%).

$^1$H NMR (400 MHz, CDCl$_3$) δ [ppm]: 7.76-6.82 (16H, m, DMTr and aromatic protons), 4.69 and 4.34 (4H, s, —CH$_2$—O—), 3.79 (6H, s, H-methoxy), 1.58 (2H, s, OH)

$^{13}$C NMR (100 MHz, CDCl$_3$) δ [ppm]: 158.51, 158.38, 157.59, 144.77, 137.27, 135.93, 130.01, 128.07, 127.89, 126.85, 119.35, 118.56, 113.18, 86.67, 66.56, 63.62, 55.20

Mass (FAB) m/z: 442 ([M$^+$+H]), 303, 277, 185, 93, 57.

HRMS (FAB) Calcd for C$_{28}$H$_{28}$NO$_4$
442.20183 Found 442.20332.

21

Preparation Example of Compounds 17 and 18: CPG resin bearing a dimethyl pyridinecarboxylate derivative To a solution of the compound (16) (0.20 g, 0.45 mmol) in pyridine (4.5 mL) were added DMAP (1.1 mg, 0.009 mmol, 0.02 eq.) and succinic anhydride (136 mg, 1.36 mmol, 3 eq.), and stirred for 17 hours under Ar atmosphere. Then, TLC (Hex:EtOAc=1:1) was used to confirm the progress of the reaction. The reaction mixture was subjected to extraction with EtOAc and sat. NaHCO₃ aq. The organic layer was washed with sat. NaCl aq., dried over anhydrous sodium sulfate, evaporated under reduced pressure to remove the solvent, and dried in vacuo. To the resultant concentrate (17) (0.16 g, 0.30 mmol, 66%) was added dry DMF (7.5 mL) to dissolve. To the solution was added CPG (338 mg, 0.075 mmol) and allowed to stand for 30 minutes to be mixed well. Then, to the mixture was added WSC (71 mg, 0.37 mmol, 4.9 eq.) and shaken for one day at a room temperature. In a post-processing stage, the mixture was washed with pyridine, and mixed and shaken for 16 hours with a solution of 0.1 M DMAP in pyridine:acetic anhydride (9:1) (6 mL). A modification carrier for synthesizing oligonucleotide derivative (18) of Comparative Example (1) was thus produced. The product was washed with methanol and acetone, and dried. A measured activity was 73.94 μmol/g.

Example 2

<Production of a Modification Carrier for Synthesizing Oligonucleotide Derivative Having a Benzene Ring and a Pyridine Ring Linked Via a Thiourea Bond>

In Example 2, a modification carrier for synthesizing oligonucleotide derivative having a benzene ring and a pyridine ring linked via a thiourea bond was prepared according to the following synthetic route.

22

Preparation of 3-(4,4'-dimethoxytrityloxymethyl)benzyl isothiocyanate (21)

3-(4,4'-Dimethoxytrityloxymethyl)benzylamine (5) (613 mg, 1.39 mmol), carbon disulfide (0.85 mL, 13.9 mmol, 10 eq.), and triethylamine (0.20 mL, 1.39 mmol) were dissolved in EtOH (2 mL). The air was evacuated from the reaction system, and then Ar was charged therein. The reaction mixture was stirred for 2 hours at a room temperature. Then, in an ice bath, to the mixture were added dropwise a solution of di-tert-butyl dicarbonate (3.06 mg, 1.40 mmol) in EtOH (0.6 mL) and a solution of DMAP (6.12 mg, 6 mol %) in EtOH (0.6 mL). The mixture was further stirred for 4 hours at a room temperature. TLC was used to confirm there was no starting material in the mixture. Then, the reaction mixture was evaporated under reduced pressure. The residue was purified by column chromatography (Hex:EtOAc=10:1) to isolate 3-(4,4'-dimethoxytrityloxymethyl)benzyl isothiocyanate (21) (640 mg, 96%) as a pale yellow oil.

¹H-NMR (CDCl₃, 400 MHz)
δ=7.23-7.68 (17H, m, Ar—H), 6.84 (4H, d, J=8.8 Hz, Ar—H), 4.67 (2H, s, CH₂), 4.15 (2H, s, CH₂), 3.79 (6H, s, CH₃O)

¹³C-NMR (CDCl₃, 100 MHz)
δ=158.3, 144.4, 135.4, 130.5, 130.4, 129.5, 128.9, 128.5, 126.9, 118.6, 113.7, 112.1, 111.9, 111.8, 86.4, 56.9, 55.5, 54.0

Preparation of N-[3-(4,4'-dimethoxytrityloxymethyl) benzyl]-N'-{[6-(tert-butyldimethylsilyloxymethyl) pyridin-2-yl]methyl}thiourea (22)

To a solution of 3-(4,4'-dimethoxytrityloxymethyl)benzyl isothiocyanate (21) (332 mg, 0.69 mmol) in CDCl₃ (4.6 mL)

[formula 15]

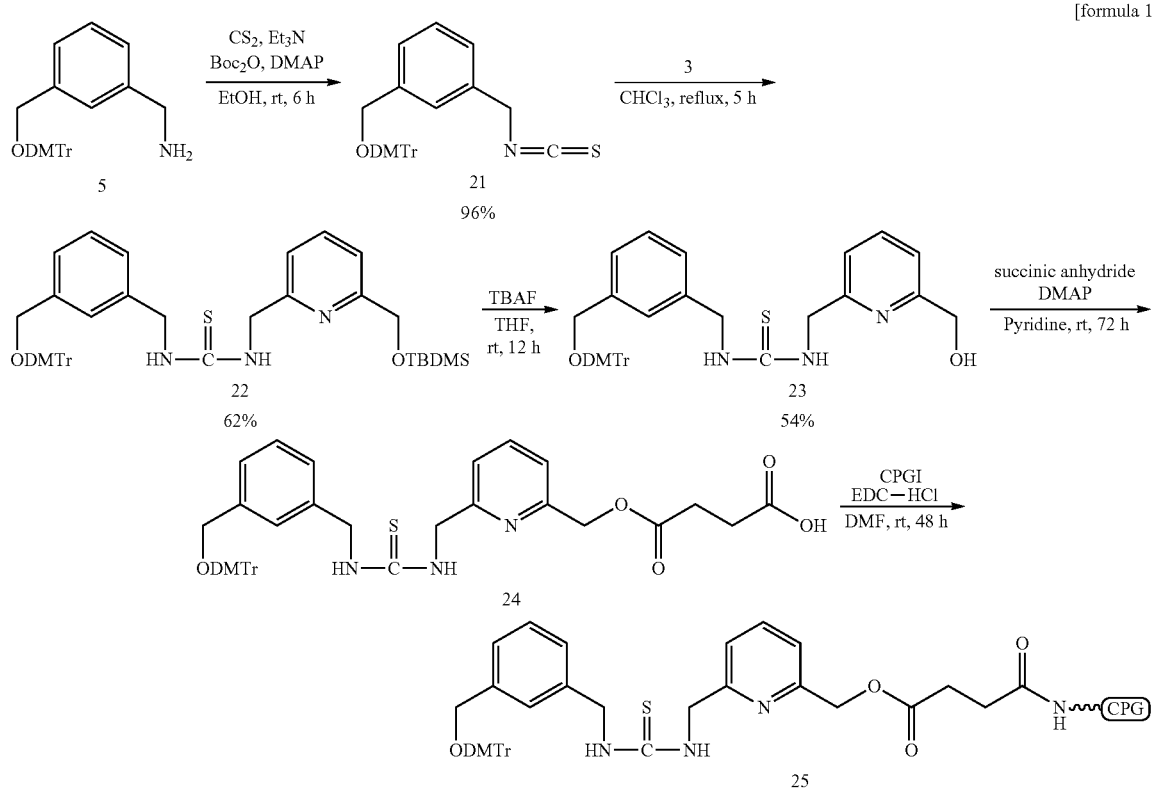

was added a solution of 2-aminomethyl-6-[(tert-butyldimethylsilyloxy)methyl]pyridine (3) (63.10 mg, 0.39 mmol) in CDCl₃ (3 mL). The air was evacuated from the reaction system, and then Ar was charged therein. The reaction mixture was refluxed for 5 hours. TLC was used to confirm there was no starting material in the mixture. Then, the reaction mixture was evaporated under reduced pressure. The residue was purified by silica gel column chromatography (Hex:EtOAc=3:1 to 2:1) to give N-[3-(4,4'-dimethoxytrityloxymethyl)benzyl]-N'-{[6-(tert-butyldimethylsilyloxymethyl)pyridin-2-yl]methyl}thiourea (22) (316 mg, 62%) as a yellow oil.

¹H-NMR (CDCl₃, 400 MHz)

δ=7.08-7.69 (17H, m, Ar—H), 6.82 (4H, d, J=6.8 Hz, Ar—H), 4.69 (4H, s, CH₂), 4.51 (2H, s, CH₂), 4.16 (2H, s, CH₂), 3.78 (6H, s, CH₃O), 0.92 (9H, s, t-C₄H₉Si), 0.05 (6H, s, (CH₃)₂Si)

¹³C-NMR (CDCl₃, 100 MHz)

δ=160.6, 158.3, 154.3, 144.8, 140.0, 137.7, 136.0, 129.9, 128.5, 128.0, 127.7, 126.6, 126.3, 126.2, 126.1, 120.3, 118.8, 113.0, 86.3, 65.3, 65.2, 55.1, 49.3, 25.7, 18.1, −5.4

Preparation of N-[3-(4,4'-dimethoxytrityloxymethyl)benzyl]-N'-[(6-hydroxymethylpyridin-2-yl)methyl]thiourea (23)

N-[3-(4,4'-Dimethoxytrityloxymethyl)benzyl]-N'-{[6-(tert-butyldimethylsilyloxymethyl)pyridin-2-yl]methyl}thiourea (22) (316 mg, 0.43 mmol) was suspended in THF (2.2 mL). The air was evacuated from the reaction system, and then Ar was charged therein. The suspension was stirred at a room temperature. To the suspension was added 1.0M TBAF in THF (0.48 mL). The mixture was further stirred for 12 hours. TLC was used to confirm there was no starting material in the mixture. Then, the reaction mixture was evaporated under reduced pressure. The residue was purified by silica gel column chromatography (CDCl₃:MeOH=200:1 to 50:1) to give N-[3-(4,4'-dimethoxytrityloxymethyl)benzyl]-N'-[(6-hydroxymethylpyridin-2-yl)methyl]thiourea (13) (141 mg, 54%) as yellow crystals.

¹H-NMR (CDCl₃, 400 MHz)

δ=7.04-7.55 (17H, m, Ar—H), 6.75 (4H, d, J=9.0 Hz, Ar—H), 4.60 (4H, s, CH₂), 4.38 (2H, s, CH₂), 4.08 (2H, s, CH₂), 3.71 (6H, s, CH₃O)

¹³C-NMR (CDCl₃, 100 MHz)

δ=183.4, 158.8, 158.4, 155.0, 144.8, 139.8, 137.7, 136.0, 130.0, 128.7, 128.0, 127.8, 126.7, 126.3, 126.1, 120.8, 119.4, 113.1, 86.4, 65.34, 64.3, 59.5, 55.1, 49.3

Preparation of a CPG Resin Bearing a Thiourea-Bonding Benzene-Pyridine Structure (25)

To a solution of N-[3-(4,4'-dimethoxytrityloxymethyl)benzyl]-N'-[(6-hydroxymethylpyridin-2-yl)methyl]thiourea (23) (141 mg, 0.23 mmol) in pyridine (3 mL) were added succinic anhydride (71 mg, 3 eq.) and DMAP (0.62 mg, 0.02 eq.), and stirred for 72 hours at a room temperature. TLC was used to confirm there was no starting material in the mixture. Then, the reaction mixture was subjected to extraction with EtOAc twice, H₂O once, and sat. NaHCO₃ aq. once. The organic layer was washed with sat. NaCl aq., dried over anhydrous Na₂SO₄, and evaporated under reduced pressure to give a succinyl compound (24). The succinyl compound (24) was dried in vacuo overnight, and dissolved in DMF (6 mL, 0.01 M to CPG). The solution was well mixed with a CPG resin (119 μmol/g) (480 mg, 0.058 mmol). To the mixture was added EDC-HCl (44 mg, 0.23 mmol), and shaken for 48 hours. The reaction mixture was washed with pyridine three times. Then, to the reaction mixture was added a 0.1 M DMAP solution (pyridine:Ac₂O=9:1) (15 mL), and shaken for 12 hours at a room temperature. The reaction mixture was washed with pyridine, EtOH, and MeCN and dried in vacuo for 12 hours to give a CPG resin bearing a thiourea-bonding structure (25). A measured activity of the CPG resin (25) was 48.3 μmol/g.

The activity was determined by placing 6 mg of dried CPG resin on a glass filter, filtering a solution of HClO₄:EtOH=3:2 through the filter, measuring an absorbance of the filtrate at UV 498 nm (wavelength of DMTr group), and substituting the value in the following equation.

$$\frac{\text{Abs. (498 nm)} \times \textit{Vol.} \text{ (solution) (mL)} \times 14.3}{\text{Weight (support) (mg)}} = \text{Activity} \qquad \text{[equation 2]}$$

Example 3

<Production of a Modification Carrier for Synthesizing Oligonucleotide Derivative Having Pyridine Rings Linked Via a Thiourea Bond>

In Example 3, a modification carrier for synthesizing oligonucleotide derivative having pyridine rings linked via a thiourea bond 31 was prepared according to the following synthetic route.

[formula 16]

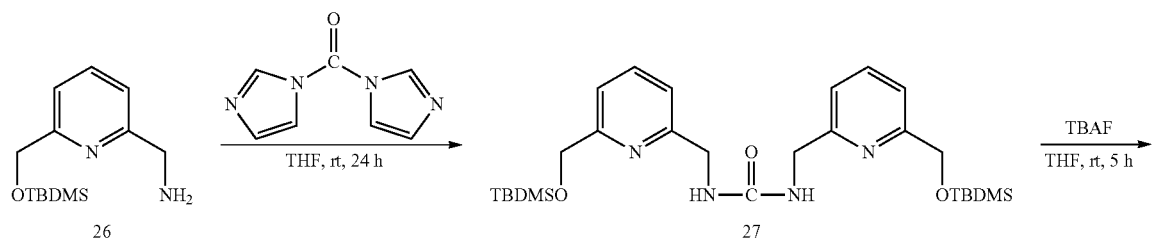

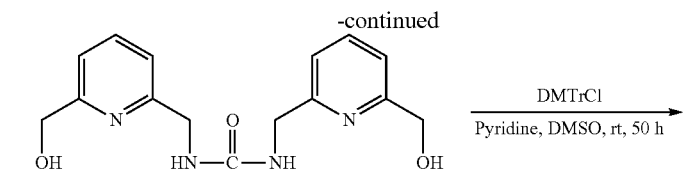
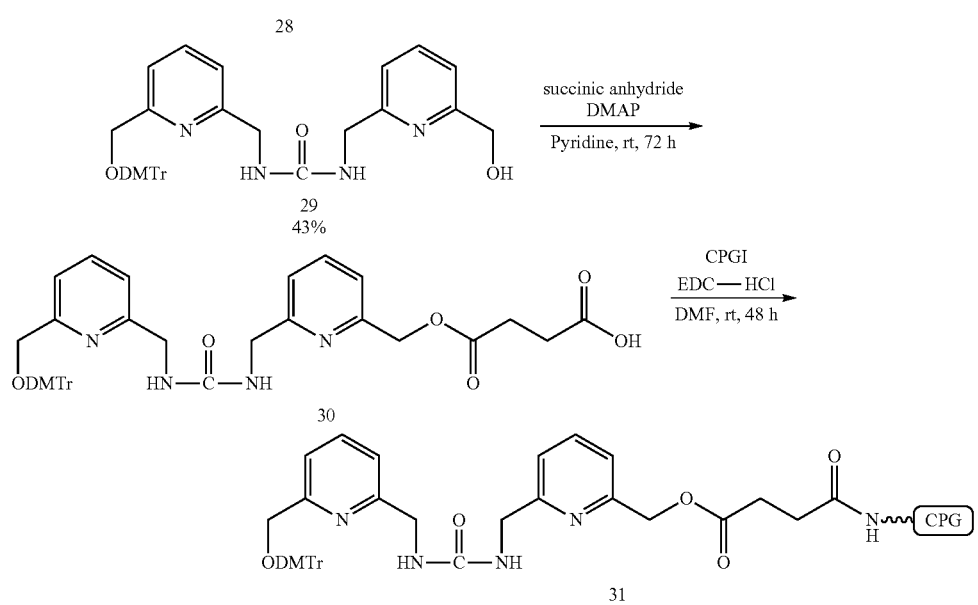

Preparation of N,N'-bis{[6-(tert-butyldimethylsilyloxy)methylpyridin-2-yl]methyl}urea (27)

2-Aminomethyl-6-[(tert-butyldimethylsilyloxy)methyl]pyridine (26) (380 mg, 1.50 mmol) and 1,1'-carbonyldiimidazole (150 mg, 0.92 mmol) were suspended in THF (10 mL). The air was evacuated from the reaction system, and then Ar was charged therein. The suspension was stirred for 24 hours at a room temperature. TLC was used to confirm there was no starting material in the mixture. Then, the reaction mixture was evaporated under reduced pressure. The residue was purified by silica gel column chromatography (CDCl$_3$:MeOH=50:1) to give N,N'-bis{[6-(tert-butyldimethylsilyloxy)methylpyridin-2-yl]methyl}urea (27) (384 mg, 96%) as yellow crystals.

$^1$H-NMR (CDCl$_3$, 400 MHz)
δ=7.66 (2H, t, J=8.0 Hz, Ar—H), 7.38 (2H, d, J=7.6 Hz, Ar—H), 7.14 (2H, d, J=7.2 Hz, Ar—H), 4.78 (4H, s, CH$_2$O), 4.49 (4H, s, CH$_2$N), 0.96 (18H, s, t-C$_4$H$_9$Si), 0.12 (12H, s, (CH$_3$)$_2$Si)

$^{13}$C-NMR (CDCl$_3$, 100 MHz)
δ=160.7, 158.2, 156.6, 137.3, 119.8, 118.3, 65.9, 45.6, 25.8, 18.3, −5.4

Preparation of N,N'-Bis{[6-(hydroxymethyl)pyridin-2-yl]methyl}urea (28)

N,N'-Bis{[6-(tert-butyldimethylsilyloxy)methylpyridin-2-yl]methyl}urea (27) (855 mg, 1.61 mmol) was suspended in THF (8.1 mL). The air was evacuated from the reaction system, and then Ar was charged therein. The suspension was stirred at a room temperature. To the suspension was added dropwise 1.0M TBAF in THF (3.7 mL), and further stirred for 5 hours. TLC was used to confirm there was no starting material in the mixture. Then, the reaction mixture was evaporated under reduced pressure. The residue was suction-filtered to give N,N'-bis{[6-(hydroxymethyl)pyridin-2-yl]methyl}urea (28) (812 mg) as white crystals.

$^1$H-NMR (DMSO-d$_6$, 400 MHz)
δ=7.73 (2H, t, J=7.8 Hz, Ar—H), 7.30 (2H, d, J=7.8 Hz, Ar—H), 7.13 (2H, d, J=7.6 Hz, Ar—H), 6.72 (2H, t, J=5.8 Hz, NH), 5.38 (2H, t, J=5.8 Hz, OH), 4.53 (4H, d, J=5.6 Hz, CH$_2$), 4.28 (4H, d, J=5.8 Hz, CH$_2$)

$^{13}$C-NMR (DMSO-d$_6$, 100 MHz)
δ=161.1, 158.7, 158.0, 137.0, 118.7, 118.1, 64.1, 44.8

Preparation of N-{[3-(4,4'-Dimethoxytrityloxymethyl)pyridin-2-yl]methyl}-N'-[(6-hydroxymethylpyridin-2-yl) methyl]urea (29)

N,N'-Bis{[6-(hydroxymethyl)pyridin-2-yl]methyl}urea (28) (812 mg) and DMTrCl (271 mg, 0.8 mmol) were added in pyridine (6 mL) and DMSO (1.2 mL). The mixture was heated (40° C.) to form a suspension. The air was evacuated from the reaction system, and then Ar was charged therein. The suspension was stirred for 12 hours at a room temperature. As checked by TLC, the reaction hardly progressed (almost all spots corresponded to starting materials). Then, to the suspension was further added DMTrCl (405 mg, 1.2 mmol), and stirred for additional 12 hours. As checked by TLC, the reaction progressed, but starting materials remained (a spot of product became dark, but there were still spots of starting materials). Then, to the reaction mixture was further added DMTrCl (405 mg, 1.2 mmol), and stirred for additional 26 hours. The reaction was confirmed to further progress, and quenched. The reaction mixture was subjected to extraction with sat. NaHCO$_3$ aq. once, EtOAc twice, H$_2$O once, and sat. NaHCO$_3$ aq. once. The organic layer was dried over anhydrous Na$_2$SO$_4$, and evaporated under reduced pressure to remove the solvent. The residue was purified by silica gel column chromatography (CHCl$_3$:MeOH=20:1) to isolate N-{[3-(4,4'-dimethoxytrityloxymethyl)pyridin-2-yl]methyl}-N'-[6-hydroxymethylpyridin-2-yl)methyl]urea (29) (424 mg, 43%) as pale-yellow crystals.

$^1$H NMR (CDCl$_3$, 400 MHz)=

δ=7.62-6.96 (m, 15H, Ar—H), 6.74 (d, 4H, J=9.0 Hz, Ar—H), 4.52 (s, 2H, CH$_2$), 4.33 (d, 4H, J=5.6 Hz, CH$_2$), 4.20 (s, 2H, CH$_2$), 3.70 (s, 6H, CH$_3$O)

Preparation of Modification Carrier for Synthesizing Oligonucleotide Derivative Having Pyridine Rings Linked Via a Thiourea Bond (31)

To a solution of N-{[3-(4,4'-Dimethoxytrityloxymethyl) pyridin-2-yl]methyl}-N'-[6-hydroxymethylpyridin-2-yl)methyl]urea (29) (363 mg, 0.60 mmol) in pyridine (7.8 mL) were added succinic anhydride (185 mg, 3 eq.) and DMAP (1.62 mg, 0.02 eq.), and stirred for 72 hours at a room temperature. TLC was used to confirm that there was no starting material in the mixture. Then, the reaction mixture was subjected to extraction with EtOAc twice, H$_2$O once, and sat. NaHCO$_3$ aq. once. The organic layer was washed with sat. NaCl aq., dried over anhydrous Na$_2$SO$_4$, and evaporated under reduced pressure to give a succinyl compound (24). The succinyl compound (30) was dried in vacuo overnight, and dissolved in DMF (15.6 mL, 0.01 M to CPG). The solution was well mixed with a CPG resin (119 µmol/g) (1.25 g, 0.15 mmol). To the mixture was added EDC-HCl (115 mg, 0.60 mmol), and shaken for 48 hours. The reaction mixture was washed with pyridine three times. Then, to the reaction mixture was added a 0.1 M DMAP solution (pyridine:Ac$_2$O=9:1) (15 mL), and shaken for 12 hours at a room temperature. The reaction mixture was washed with pyridine, EtOH, and MeCN, and dried in vacuo for 12 hours to give a CPG resin product. A measured activity of the product was 79.91 µmol/g.

The activity was determined by placing 6 mg of dried CPG resin on a glass filter, filtering a solution of HClO$_4$:EtOH=3:2 through the filter, measuring an absorbance of the filtrate at UV 498 nm (wavelength of DMTr group), and substituting the value in the following equation.

<Synthesis of siRNA>

Modification carrier for synthesizing oligonucleotide derivative of Examples 1 to 3 and Comparative Example 1 thus produced were used to synthesize oligonucleotide derivatives having a sequence (which targets Renilla Luciferase) and an artificial 3'-dangling end as shown in Table 1 by phosphoramidite solid-phase synthesis in an automatic nucleic acid synthesis. A native siRNA having a 3'-TT end was also synthesized in the same way. Sequences of synthesized oligonucleotides are shown in Table 4.

Synthesis and purification of oligonucleotide in siRNA synthesis will be described in detail bellow.

Synthesis of oligonucleotide employed the following phosphoramidite method with an automatic nucleic acid synthesizer:

1, removing a dimethoxytrityl (DMTr) group protecting the 3'-end of an oligonucleotide chain (fixed on a solid CPG carrier via a linking group at the 3'-end) from the oligonucleotide chain with an acid, 2, connecting a 3'-phosphoramidite-deoxynucleotide derivative to the formed free 5'-end, in which, tetrazole was used as an activator for an amidite, 3, capping an unreacted 5'-end by acetylation to inhibit further coupling, thereby ensuring no oligonucleotide elongating improperly, and 4, oxidizing the phosphite triester formed by coupling to a phosphate triester, resulting in an oligonucleotide chain having one more nucleotides than the starting chain having.

According to the phosphoramidite method, an oligonucleotide was synthesized on a 1 µmol scale. A 3400 DNA automatic synthesizer was used. Phosphoramidite derivatives of A, G, C, and U were each dissolved in MeCN to form respective 0.1 M solutions. A prepared artificial dangling end-carrying resin was dissolved in MeCN and adjusted to 0.12 M. Synthesis of the oligonucleotide was terminated at the state that the oligonucleotide had the 5'-end not protected with a DMTr group. The CPG resin was dried in Ar gas stream. The synthesized oligonucleotide bonded to the CPG resin was transferred to an Eppendorf tube. To this was added 1.2 mL of aqueous solution of EtOH:NH$_4$OH=3:1, and shaken for 12 hours at a room temperature to cut out from the resin and remove a benzoyl group for deprotection. Then, the solution was dried to solid under reduced pressure. To the residue was added 1 mL of 1M TBAF in THF, and shaken for 12 hours to remove a silyl group for deprotection. The resulting solution was diluted to 30 mL with 0.1 M TEAA buffer (*1), and passed through an equilibrated C-18 reverse-phase column (Sep-Pak) to adsorb the product to the column (for conditioning, before the solution was applied, 10 mL of MeCN and 15 mL of 0.1 M TEAA buffer were passed through the column.)

The column was washed with sterile water for removing salts. The product was eluted with 3 mL of 50% MeCN in H$_2$O. The eluate was dried to solid under reduced pressure. The residue was mixed with 200 µL of loading solution (1×TBE in 90% formamide) and subjected to polyacrylamide gel electrophoresis on 20% gel (500 V, 20 mA) (*2). An area containing an intended oligonucleotide was cut out from the gel, and immersed and shaken in an eluting solution (1 mL of 2 N TEAA buffer, 0.2 mL of 0.1 mM EDTA in water, and H$_2$O were mixed such that a volume was 20 mL) overnight. The eluate was again passed through an equilibrated C-18 reverse-phase column (Sep-Pak) for purification.

(*1) Preparation of 20% polyacrylamide gel containing 7 M urea 45 mL of 40% acrylamide solution$^{(*1-1)}$, 37.8 g of urea, and 8 mL of 10×TBE buffer$^{(*1-2)}$ were mixed and dissolved. To this was added H$_2$O such that a volume was 80 mL. Then, 55 mg of APS was dissolved in the solution, and 40 µL of TEMED was mixed in with the solution. The solution was poured into a space between two glass plates holding a spacer (1.5 mm) inserted therebetween, and allowed to stand for 1 or more hours to solidify. 1-fold TBE buffer$^{(*1-3)}$ was used as an electrophoresis buffer.

(*1-1) 40% acrylamide: 190 g of acrylamide and 10 g of N,N'-bisacrylamide were dissolved in H$_2$O such that a volume was 500 mL.

(*1-2) 10×TBE buffer: 108 g of Tris, 55 g of boric acid, and 7.43 g of EDTA.2Na were dissolved in H$_2$O such that a volume was 1 L.

(*1-3) 1×TBE buffer: tenfold dilution of 10×TBE buffer, prepared in use.

(*2)

2N TEAA buffer: 1 L solution of 277.6 mL of triethylamine in water, adjusted to pH 7.0 with acetic acid 0.1M TEAA buffer: twentyfold dilution of 2N TEAA buffer, prepared in use.

0.1 M EDTA aqueous solution: hundredfold dilution of 40 mL solution of 1.81 g of EDTA.4Na in water, prepared in use.

Each sample thus prepared was dissolved in 1 mL of H$_2$O. A dilution was used to measure an absorbance of the sample at 260 nm to determine a yield of the sample.

A molecular weight of each sample was determined by MALDI-TOF/MASS. Results are shown in Table 1.

TABLE 1

| synthetic oligonucleotide | calculated | observed |
|---|---|---|
| TT-antisense | 6808.9 | 6807.6 |
| TT-sense | 6499.8 | 6502.6 |
| BuP-antisense | 6563.9 | 6568.4 |
| BuP-sense | 6254.8 | 6254.0 |
| PuP-antisense | 6570.1 | 6567.3 |
| PuP-sense | 6260.8 | 6258.9 |
| BtuP-antisense | 6585.2 | 6581.7 |
| BtuP-sense | 6275.9 | 6273.1 |

Each sample was further purified by HPLC. Buffers used were as follows. A C-18 column was used.

Buffer Composition

A buffer: MeCN in 0.1 M TEAA (pH 7.0)
B buffer: 50% MeCN in 0.1 M TEAA (pH 7.0)

<Evaluation of siRNA>

(Thermal Stability)

An siRNA strand thus synthesized using the modification carrier for synthesizing oligonucleotide derivative (9) of Example 1 (hereinafter, referredtoas"siRNA(BuP)") and a siRNA strand thus synthesized using the modification carrier for synthesizing oligonucleotide derivative (18) of Comparative Example 1 were annealed with respective complementary strands to form two double-strands (TT-antisense and TT-sense, BUP-antisense and BUP-sense). These two double-strand siRNAs were measured about a half melting temperature Tm (° C.). More specifically, for each synthesized oligonucleotide, each 600 pmol of synthesized oligonucleotide and complementary strand were dried to solid, dissolved in 200 µl, of measurement buffer (10 mM $NaH_2PO_4$—$Na_2HPO_4$ and 100 mM NaCl (pH 7.0)) to give a 3 µM solution. The solution was heated for 5 minutes to 90° C., allowed to stand for 1 or more hours to hybridize, and deaerated. 170 µL of the resultant sample was placed in a special cell and measured about an absorbance at 260 nm with varying temperature in a Tm determination apparatus. A chart of measured absorbance was used to calculate a half melting temperature (Tm) by a median line method. Results showed that BP, BuP, PuP, and BtuP samples were nearly equal to the native TT sample in thermal stability, as shown in FIG. 5 and Table 2.

TABLE 2

| XX | Tm (° C.) | ΔTm (° C.) |
|---|---|---|
| TT | 80.15 | — |
| BP | 78.84 | −1.31 |
| BuP | 78.60 | −1.55 |
| PuP | 77.79 | −2.36 |
| BtuP | 77.78 | −2.37 |

(Measurement of Effects for Suppressing Expression of Protein)

For evaluating effects for suppressing expression of protein, the siRNA strand synthesized using the modification carrier for synthesizing oligonucleotide derivative (9) of Example 1 (siRNA(BuP)) and the siRNA strand synthesized using the modification carrier for synthesizing oligonucleotide derivative (18) of Comparative Example 1 (hereinafter, referred to as "siRNA(BP)") were subjected to the Dual Luciferase (trademark) assay at concentrations of 0.1 nM, 1.0 nM, and 10 nM, and examined for the effect of knockdown. Each synthesized siRNA strand targeted a gene of Renilla luciferase and its effect of knockdown was measured through transfection of a HeLa cell with the synthesized siRNA strand and a vector expressing this gene and a control gene (firefly luciferase) together.

The assay uses a vector expressing both luminescent proteins, a Firefly and a Renilla luciferases, and measures a luminescence ratio of these luciferases to calculate a degree of suppression of Renilla luciferase expression by siRNA for evaluation (see FIG. 6).

More specifically, a HeLa cell culture was adjusted to 4000 cell/ml, put in each well of a 96-well plate in an amount of 100 µl, and cultured for 24 hours. Synthesized siRNA strands were each dissolved in TE buffer (100 mM NaCl) and annealed. Each annealed siRNA strand was mixed with a culture medium (OPTI-MEM), 1 µl of 0.1 µg/µl psi-CHECK (a vector having both sequences of Firefly and Renilla luciferases), and 1.5 µl of TransFast (trademark) (transfection reagent) such that the total volume was 175 µl. Each mixture was put in wells of the 96-well plate, from which a culture medium had been sucked out, in an amount of 35 µl per well. After 1 hour, 100 µl of culture medium was added to each well, and cultured for 24 hours. Then, the culture medium was sucked out, and the plate was stored in a freezer. In measurement, the plate was thawed, added with 24 µl of Dual glo substrate (substrate for Firefly luciferase), and allowed to stand for 10 minutes. From each well, 23 µl of sample was taken and transferred in a 96-well plate for luminescence measurement and measured about luminescence of Firefly luciferase. Then, the sample was added with 23 µl of Stop and glo substrate, allowed to stand for 10 minutes, and measured about luminescence of Renilla luciferase. The measured luminescence of Renilla luciferase was divided by that of Firefly luciferase. The quotient was compared with other quotient resulting from other sample on the basis of percentage to control. In measurement of luciferase, a Luminescenser JNR was used.

As can be seen in FIG. 7, results showed that siRNA(BuP) was comparable to siRNA(BP) having a benzene-pyridine moiety in ability to suppress protein expression.

(Measurement of Nuclease Resistance)

These synthesized siRNA(BuP), siRNA(BP), and native siRNA(TT) as described above were modified at each 5'-end with a fluorescent substituent, and examined for 3' exonuclease resistance. The fluorescent substituent was fluorescein, and was introduced at each 5'-end by the phosphoramidite method using a fluorescein-phosphoramidite derivative in an automatic DNA/RNA synthesizer.

These modified siRNAs with the fluorescent substituent at the 5'-end were examined for nuclease resistance.

More specifically, for each of fluorescein-labeled oligonucleotides (siRNA(TT), siRNA(BP), and siRNA(BuP), 300 pmol of oligonucleotide was mixed with 100 µL of SVP at $5.0 \times 10^{-3}$ unit/mL, and incubated at 37° C. At points 0 min, 1 min, 5 min, 10 min, 15 min, 30 min, 1 h, and 3 h from the mixing, 5 µL of sample was taken from the reaction mixture and transferred into a new Eppendorf tube containing 15 µL of aliquot from a reaction-quenching solution (0.1% BPB, XC in 7 M Urea) to give a reaction sample for a time equal to the point taken. A reaction sample for 0 min was prepared without the enzyme.

These samples were subjected to PAGE on 20% gel to separate products, and measured about fluorescence intensity of fluorescein with a fluorescence scanner (lumino image analyzer LAS-4000) to estimate a degree of nuclease resistance.

Results are shown in FIGS. 8 and 9. FIG. 9 shows that the native siRNA(TT) had almost no nuclease resistance as there was no undegraded strand after 1 min. In contrast, siRNA (BuP) and siRNA(BP) both having a benzene-pyridine moiety exhibited such a nuclease resistance as there was about a half of undegraded strands even after 30 minutes. These results showed excellent 3' exonuclease resistance of siRNA (BuP) and siRNA(BP) both having a benzene-pyridine moiety, compared with the native siRNA(TT).

From these results, it is also apparent that single- and double-strand DNAs, single- and double-strand RNAs, DNA/RNA chimeras, and DNA/RNA hybrids, and the like, produced with a siRNA synthesized using the modification carrier for synthesizing oligonucleotide derivative (9) of Example 1 (hereinafter, referred to as "siRNA(BuP)") will have nuclease resistance at the same level.

As described above, the modification carriers for synthesizing oligonucleotide derivative of Examples can easily produce oligonucleotide derivatives chemically modified at the 3'-end with two units each having a benzene or pyridine structure. In addition, a pyridine ring and a benzene ring can be easily and quantitatively linked via a urea bond by coupling these aromatic rings with carbonyldiimidazole. The modification carrier for synthesizing oligonucleotide derivative of the present invention is thus easily produced, compared with that by a method of production through forming a phosphate ester bond using an amidite reagent.

Example 4

<Production of Modification Carrier for Synthesizing Oligonucleotide Derivative Having Fluoromethylbenzene Rings Linked Via a Urea Bond>

In Example 4, a modification carrier for synthesizing oligonucleotide derivative having fluoromethylbenzene rings linked via a urea bond was prepared according to the following synthetic route.

[formula 17]

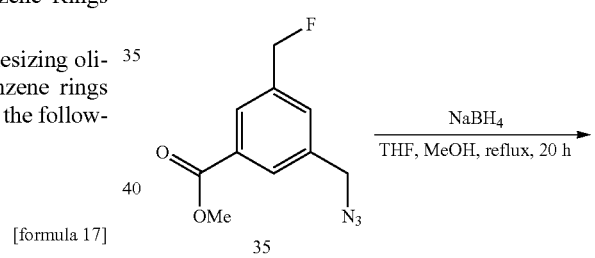

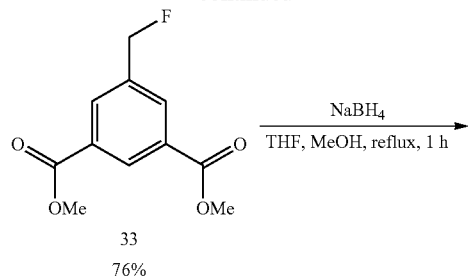

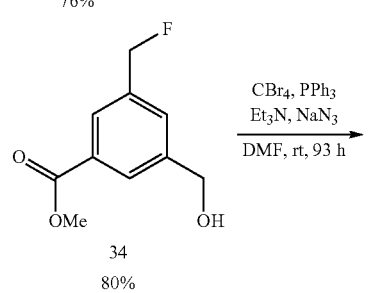

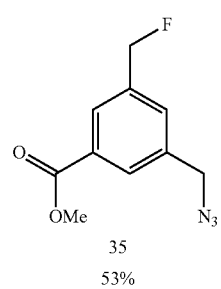

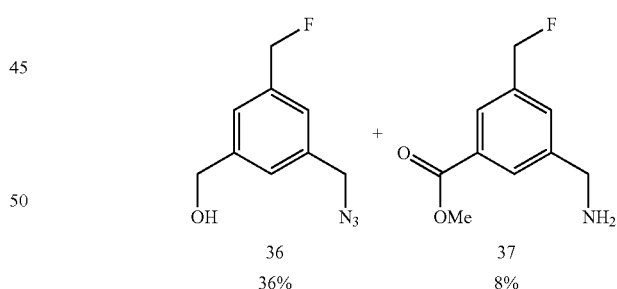

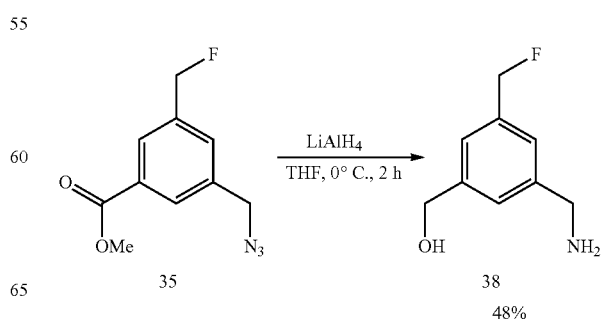

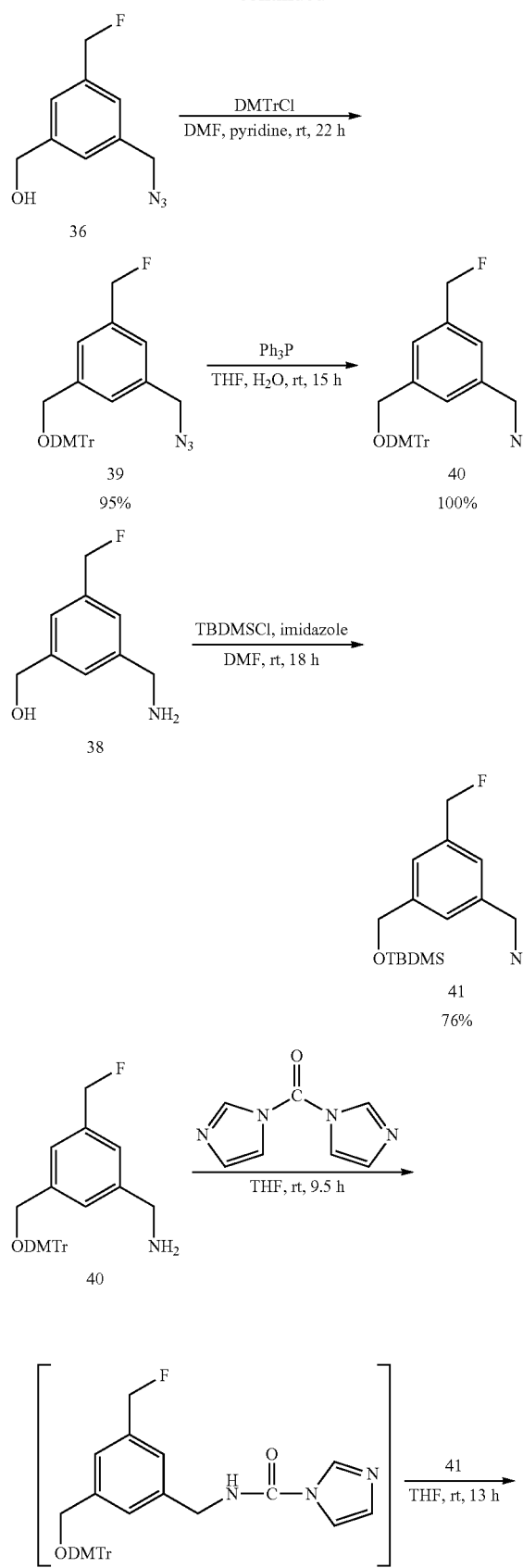

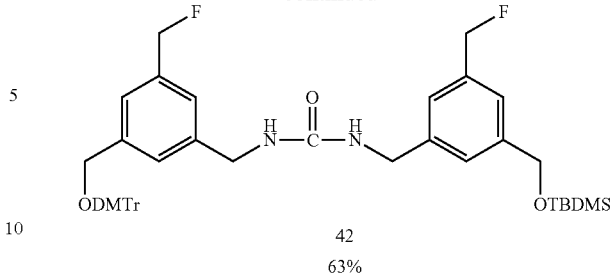

42
63%

Preparation of dimethyl 5-hydroxymethylisophthalate (32)

Trimethyl 1,3,5-benzenetricarboxylate (5.02 g, 19.9 mmol) was dissolved in THF (15 mL). The air was evacuated from the reaction system, and then Ar was charged therein. To the solution were added NaBH$_4$ (901 mg, 23.8 mmol), and then a mixed solution of THF:MeOH (12.5 mL:3.7 mL) slowly dropwise. The reaction mixture was refluxed for 30 minutes. TLC was used to confirm the progress of the reaction. Then, the reaction was quenched with HCl (1 N, 20 mL). The mixture was extracted with EtOAc. The organic layer was washed with a saturated sodium chloride aqueous solution, dried over anhydrous sodium sulfate, and evaporated under reduced pressure to remove the solvent. The residue was purified by neutral silica gel column chromatography (hexane:EtOAc=4:1 to 3:1) to isolate dimethyl 5-hydroxymethylisophthalate (32) (2.73 g, 61%) as white crystals.

$^1$H-NMR (CDCl$_3$, 400 MHz)
δ=8.60 (1H, s, Ar—H), 8.24 (2H, s, Ar—H), 4.82 (2H, d, J=6.3 Hz, CH$_2$O), 3.95 (6H, s, CH$_3$CO$_2$), 1.98 (1H, t, J=6.3 Hz, OH)
$^{13}$C-NMR (CDCl$_3$, 100 MHz)
δ=166.2, 142.0, 131.9, 130.7, 129.7, 64.05, 52.37

Preparation of dimethyl 5-fluoromethylisophthalate (33)

Under Ar atmosphere, with ice-cooled, to a solution of dimethyl 5-hydroxymethylisophthalate (32) (3.36 g, 15.0 mmol) in CH$_2$Cl$_2$ (150 mL, 0.1 M solution) was slowly added dropwise (diethylamino)sulfur trifluoride (4.00 mL, 30.5 mmol), and stirred for 2 hours at a room temperature. TLC was used to confirm the progress of the reaction. Then, the reaction was quenched with MeOH (150 mL). The solvent was removed under reduced pressure. The residue was subjected to extraction with EtOAc and a saturated sodium hydrogen carbonate aqueous solution (three times). The organic layer was washed with a saturated sodium chloride aqueous solution, dried over anhydrous sodium sulfate, and evaporated under reduced pressure to remove the solvent. The residue was purified by neutral silica gel column chromatography (hexane:EtOAc=10:1) to isolate dimethyl 5-fluoromethylisophthalate (33) (2.57 g, 78%) as white crystals.

$^1$H-NMR (CDCl$_3$, 400 MHz)
δ=8.67 (1H, s, Ar—H), 8.24 (2H, s, Ar—H), 5.48 (2H, d, J=48.1 Hz, CH$_2$F), 3.97 (6H, s, CH$_3$CO$_2$)
$^{13}$C-NMR (CDCl$_3$, 100 MHz)
δ=165.8, 137.3 (d, J=19.1 Hz), 132.2 (d, J=6.7 Hz), 131.1, 130.8, 83.2 (d, J=171.7 Hz), 52.5

Preparation of methyl 3-fluoromethyl-5-hydroxymethylbenzoate (34)

Dimethyl 5-fluoromethylisophthalate (33) (3.16 g, 14.0 mmol) was dissolved in THF (10.5 mL). The air was evacuated from the reaction system, and then Ar was charged therein. To the solution were added NaBH$_4$ (638 mg, 16.9 mmol), and then a mixted solution of THF:MeOH (8.8 mL:2.6 mL) slowly dropwise. The reaction mixture was refluxed for 1 hour. TLC was used to confirm the progress of the reaction. Then, the reaction was quenched with HCl (1 N, 14 mL). The mixture was extracted with EtOAc. The organic layer was washed with a saturated sodium chloride aqueous solution, dried over anhydrous sodium sulfate, and evaporated under reduced pressure. The residue was purified by neutral silica gel column chromatography (hexane:EtOAc=5:1 to 2:1) to isolate methyl 3-fluoromethyl-5-hydroxymethylbenzoate (34) (2.21 g, 80%) as white crystals.

$^1$H-NMR (CDCl$_3$, 400 MHz)
δ=7.93 (1H, s, Ar—H), 7.87 (1H, s, Ar—H), 7.52 (1H, s, Ar—H), 5.36 (2H, d, J=48.6 Hz, CH$_2$F), 4.67 (2H, s, CH$_2$O), 3.88 (3H, s, CH$_2$CO$_2$)

$^{13}$C-NMR (CDCl$_3$, 100 MHz)
δ=166.6, 141.9, 136.7 (d, J=18.1 Hz), 130.3, 129.8 (d, J=5.7 Hz), 127.8 (d, J=1.9 Hz), 127.1 (d, J=6.7 Hz), 83.6 (d, J=169.8 Hz), 63.8, 52.1

Preparation of methyl
3-azidomethyl-5-fluoromethylbenzoate (35)

Methyl 3-fluoromethyl-5-hydroxymethylbenzoate (34) (2.30 g, 11.6 mmol) was dried for 24 hours. Sodium azide (3.77 g, 58.1 mmol), carbon tetrabromide (4.24 g, 12.1 mmol), and triphenylphosphine (3.66 g, 13.9 mmol) were dried for 48 hours. Under Ar atmosphere, these were mixed with triethylamine (3.6 mL), dissolved in DMF (88 mL), and stirred for 93 hours at a room temperature. TLC was used to confirm the progress of the reaction. Then, the mixture was extracted with EtOAc. The organic layer was washed with a saturated sodium chloride aqueous solution, dried over anhydrous sodium sulfate, and evaporated under reduced pressure to remove the solvent. The residue was purified by neutral silica gel column chromatography (hexane:EtOAc=10:1) to isolate methyl 3-azidomethyl-5-fluoromethylbenzoate (35) (1.37 g, 53%) as a pale yellow oil.

$^1$H-NMR (CDCl$_3$, 400 MHz)
δ=8.02 (1H, s, Ar—H), (8.00 1H, s, Ar—H), 7.55 (1H, s, Ar—H), 5.45 (2H, d, J=48.1 Hz, CH$_2$F), 4.45 (2H, s, CH$_2$N$_3$), 3.95 (3H, s, CH$_3$CO$_2$)

$^{13}$C-NMR (CDCl$_3$, 100 MHz)
δ=166.2, 137.5 (d, J=18.1 Hz), 136.5, 131.2, 130.9 (d, J=5.7 Hz), 129.3, 128.0 (d, J=6.7 Hz), 84.0 (d, J=171.7 Hz), 77.50, 54.1, 52.4

Preparation of
3-azidomethyl-5-fluoromethylbenzylalcohol (36)

Methyl 3-azidomethyl-5-fluoromethylbenzoate (35) (468 mg, 2.10 mmol) was dissolved in THF (1.5 mL). The air was evacuated from the reaction system, and then Ar was charged therein. To the solution were added NaBH$_4$ (97.5 mg, 2.58 mmol), and then a mixed solution of THF:MeOH (1.3 mL:0.4 mL) slowly dropwise. The reaction mixture was refluxed for 20 hour. TLC was used to confirm the progress of the reaction. Then, the reaction was quenched with 1N hydrochloric acid (2.5 mL). The mixture was extracted with EtOAc. The organic layer was washed with a saturated sodium chloride aqueous solution, dried over anhydrous sodium sulfate, and evaporated under reduced pressure to remove the solvent. The residue was purified by neutral silica gel column chromatography (hexane:EtOAc=5:1, then EtOAc) to isolate 3-azidomethyl-5-fluoromethylbenzylalcohol (36) (149 mg, 36%) as a colorless oil. In addition, the aqueous layer of the extraction was basified with a saturated sodium hydrogen carbonate aqueous solution and extracted with EtOAc. The organic layer was washed with a saturated sodium chloride aqueous solution, dried over anhydrous sodium sulfate, and evaporated under reduced pressure to give methyl 3-aminomethyl-5-fluoromethylbenzoate (37) (33.1 mg, 8%) as a yellow clear oil.

3-Azidomethyl-5-fluoromethylbenzylalcohol (36)

$^1$H-NMR (CDCl$_3$, 400 MHz)
δ=7.36 (1H, s, Ar—H), 7.33 (1H, s, Ar—H), 7.26 (1H, s, Ar—H), 5.40 (2H, d, J=48.6 Hz, CH$_2$F), 4.75 (2H, s, CH$_2$O), 4.38 (2H, s, CH$_2$N$_3$)

Methyl 3-aminomethyl-5-fluoromethylbenzoate (37)

$^1$H-NMR (CDCl$_3$, 400 MHz)
δ=7.99 (1H, s, Ar—H), 7.93 (1H, s, Ar—H), 7.56 (1H, s, Ar—H), 5.42 (2H, d, J=48.1 Hz, CH$_2$F), 3.96 (2H, s, CH$_2$N), 3.93 (3H, s, CH$_3$CO$_2$)

Preparation of
3-aminomethyl-5-fluoromethylbenzylalcohol (38)

Methyl 3-azidomethyl-5-fluoromethylbenzoate (35) (476 mg, 2.13 mmol) was dissolved in THF (21.3 mL). The air was evacuated from the reaction system, and then Ar was charged therein. In another recovery flask filled with Ar, LiAlH$_4$ (408 mg, 10.7 mmol) was placed. To this was added THF (21.3 mL) with ice-cooling to give a suspension. To the suspension was added dropwise the solution of the compound (35), and stirred for 2 hours at 0° C. TLC was used to confirm there was no starting material in the mixture. Then, the reaction was quenched with MeOH (10 mL). The mixture was filtered through cerite to remove metals. The filtrate was evaporated under reduced pressure. The residue was purified by neutral silica gel column chromatography (hexane:EtOAc=1:1, then EtOAc:MeOH=2:1) to isolate 3-aminomethyl-5-fluoromethylbenzylalcohol (38) (172 mg, 48%) as a yellow solid.

$^1$H-NMR (CD$_3$OD, 400 MHz)
δ=7.43 (2H, s, Ar—H), 7.39 (1H, s, Ar—H), 5.40 (2H, d, J=49.0 Hz, CH$_2$F), 4.66 (2H, s, CH$_2$O), 4.11 (2H, s, CH$_2$N)

$^{13}$C-NMR (CD$_3$OD, 100 MHz)
δ=144.5, 139.0 (d, J=17.2 Hz), 135.4, 128.6, 127.7 (d, J=6.7 Hz), 127.3 (d, J=5.7 Hz), 85.1 (d, J=168.8 Hz), 64.4, 44.0

Preparation of 3-(4,4'-Dimethoxytrityloxy)methyl-5-fluoromethylbenzylazide (39)

From a reaction system containing 3-Azidomethyl-5-fluoromethylbenzylalcohol (36) (142 mg, 0.73 mmol), the air was evacuated and then Ar was charged therein. To this were added DMTrCl (323 mg, 0.95 mmol), DMF (2.0 mL), and pyridine (2.0 mL), and stirred for 22 hours at a room temperature. TLC was used to confirm the progress of the reaction. Then, the solvent was removed in vacuo. The residue was subjected to extraction with EtOAc. The organic layer was washed with a saturated sodium chloride aqueous solution, dried over anhydrous sodium sulfate, and evaporated under reduced pressure to remove the solvent. The residue was purified by neutral silica gel column chromatography (hexane:EtOAc=20:1 to 5:1) to isolate
3-(4,4'-dimethoxytrityloxy)methyl-5-fluoromethylbenzylazide (39) (346 mg, 95%) as a colorless clear oil.

$^1$H-NMR (CDCl$_3$, 400 MHz)

δ=7.51-7.21 (12H, m, Ar—H), 6.84 (4H, d, J=9.2 Hz, Ar—H), 5.39 (2H, d, J=48.6 Hz, CH$_2$F), 4.37 (2H, s, CH$_2$N$_3$), 4.21 (2H, s, CH$_2$O), 3.80 (6H, s, CH$_3$O)

$^{13}$C-NMR (CDCl$_3$, 100 MHz)

δ=158.5, 144.8, 140.6, 136.9 (d, J=18.1 Hz), 136.0, 135.9, 130.0, 128.1, 127.9, 126.8, 125.7, 125.7, 113.2, 86.6, 84.2 (d, J=169.8 Hz), 65.1, 55.2, 54.5

Preparation of 3-(4,4'-dimethoxytrityloxy)methyl-5-fluoromethylbenzylamine (40)

To a solution of 3-(4,4'-dimethoxytrityloxy)methyl-5-fluoromethylbenzylazide (39) (247 mg, 0.50 mmol) in THF (5.00 mL) were added water (0.20 mL) and then triphenylphosphine (264 mg, 1.01 mmol). The air was evacuated from the reaction system, and then Ar was charged therein. The reaction mixture was stirred for 15 hours at a room temperature. TLC was used to confirm the progress of the reaction. Then, the reaction mixture was extracted with EtOAc. The organic layer was washed with a saturated sodium chloride aqueous solution, dried over anhydrous sodium sulfate, and evaporated under reduced pressure to remove the solvent. The residue was purified by neutral silica gel column chromatography (EtOAc, then EtOAc: MeOH=2:1) to isolate 3-(4,4'-dimethoxytrityloxy)methyl-5-fluoromethylbenzylamine (40) (234 mg, 100%) as a white opaque oil.

$^1$H-NMR (CDCl$_3$, 400 MHz)

δ=7.51-7.20 (12H, m, Ar—H), 6.84 (4H, d, J=8.7 Hz, Ar—H), 5.38 (2H, d, J=49.0 Hz, CH$_2$F), 4.18 (2H, s, CH$_2$O), 3.89 (2H, s, CH$_2$N), 3.79 (6H, s, CH$_3$O)

$^{13}$C-NMR (CDCl$_3$, 100 MHz)

δ=158.5, 144.9, 143.4, 140.1, 136.5 (d, J=17.2 Hz), 136.1, 130.0, 128.1, 127.8, 126.8, 126.1, 125.0 (d, J=5.7 Hz), 124.6 (d, J=6.7 Hz), 113.1, 86.5, 84.6 (d, J=168.8 Hz), 65.3, 55.2, 46.2

Preparation of 3-(t-butyldimethylsilyloxy)methyl-5-fluoromethylbenzylamine (41)

3-Aminomethyl-5-fluoromethylbenzylalcohol (38) (520 mg, 3.07 mmol) and imidazole (923 mg, 13.6 mmol) were dissolved in DMF (15.5 mL). The air was evacuated from the reaction system, and then Ar was charged therein. To the solution was added TBDMSCl (1.03 g, 6.83 mmol), and dissolved. Again the air was evacuated from the reaction system, and then Ar was charged therein. The mixture was stirred for 18 hours at a room temperature. TLC was used to confirm the progress of the reaction. The reaction mixture was extracted with EtOAc. The organic layer was washed with a saturated sodium chloride aqueous solution, dried over anhydrous sodium sulfate, and evaporated under reduced pressure to remove the solvent. The residue was purified by neutral silica gel column chromatography (hexane:EtOAc=1:1) to isolate 3-(t-butyldimethylsilyloxy)methyl-5-fluoromethylbenzylamine (41) (661 mg, 76%) as a colorless oil.

$^1$H NMR (CDCl$_3$, 400 MHz)

δ=7.21 (1H, s, Ar—H), 7.19 (1H, s, Ar—H), 7.11 (1H, s, Ar—H), 5.35 (2H, d, J=49.0 Hz, CH$_2$F), 4.73 (2H, s, CH$_2$O), 4.48 (2H, d, J=6.0 Hz, CH$_2$N), 0.94 (9H, s, t-C$_4$H$_9$Si), 0.10 (6H, s, (CH$_3$)$_2$Si)

Preparation of N-3-(4,4'-dimethoxytrityloxy)methyl-5-fluoromethylbenzyl-N'-3-(t-butyldimethylsilyloxy)methyl-5-fluoromethylbenzylurea (42)

3-(4,4'-Dimethoxytrityloxy)methyl-5-fluoromethylbenzylamine (40) (89.3 mg, 0.19 mmol) was placed in a recovery flask. The air was evacuated from the reaction system, and then Ar was charged therein. To this was added THF (5.0 mL), and dissolved. To the compound (40) was slowly added dropwise a solution of 1,1'-carbonyldiimidazole (33.0 mg, 0.20 mmol) in THF (5.0 mL), and stirred for 9.5 hours at a room temperature. TLC was used to confirm the progress of the reaction. To the reaction system was slowly added dropwise a solution of 3-(t-butyldimethylsilyloxy)methyl-5-fluoromethylbenzylamine (41) (54.8 mg, 0.19 mmol) in THF (1.6 mL), and stirred for 13 hours at a room temperature. TLC was used to confirm the progress of the reaction. The solvent was evaporated under reduced pressure. The residue was purified by neutral silica gel column chromatography (hexane: EtOAc=2:3, then EtOAc:MeOH=2:1) to give N-3-(4,4'-dimethoxytrityloxy)methyl-5-fluoromethylbenzyl-N'-3-(t-butyldimethylsilyloxy)methyl-5-fluoromethylbenzylurea (42) (93.5 mg, 63%) as a colorless oil.

$^1$H NMR (CDCl$_3$, 400 MHz)

δ=7.47-6.79 (19H, m, Ar—H), 5.28 (4H, d, J=49.0 Hz, CH$_2$F), 4.34 (2H, s, CH$_2$), 4.15 (2H, s, CH$_2$), 3.75 (8H, s, CH$_3$O and CH$_2$), 3.72 (2H, s, CH$_2$), 0.93 (9H, s, t-C$_4$H$_9$Si), 0.09 (6H, s, (CH$_3$)$_2$Si)

N-3-(4,4'-Dimethoxytrityloxy)methyl-5-fluoromethylbenzyl-N'-3-(t-Butyldimethylsilyloxy)methyl-5-fluoromethylbenzylurea (42) thus prepared can be used to produce the modification carrier for synthesizing oligonucleotide derivative of Example 3 in the same way as that in Examples 1 and 2.

The present invention should not be limited to embodiments and Examples of the present invention described above. Modifications and variations within the scope of the invention will readily become apparent to those skilled in the art. Such modifications and variations also form a part of the present invention.

INDUSTRIAL APPLICABILITY

Figure 1:
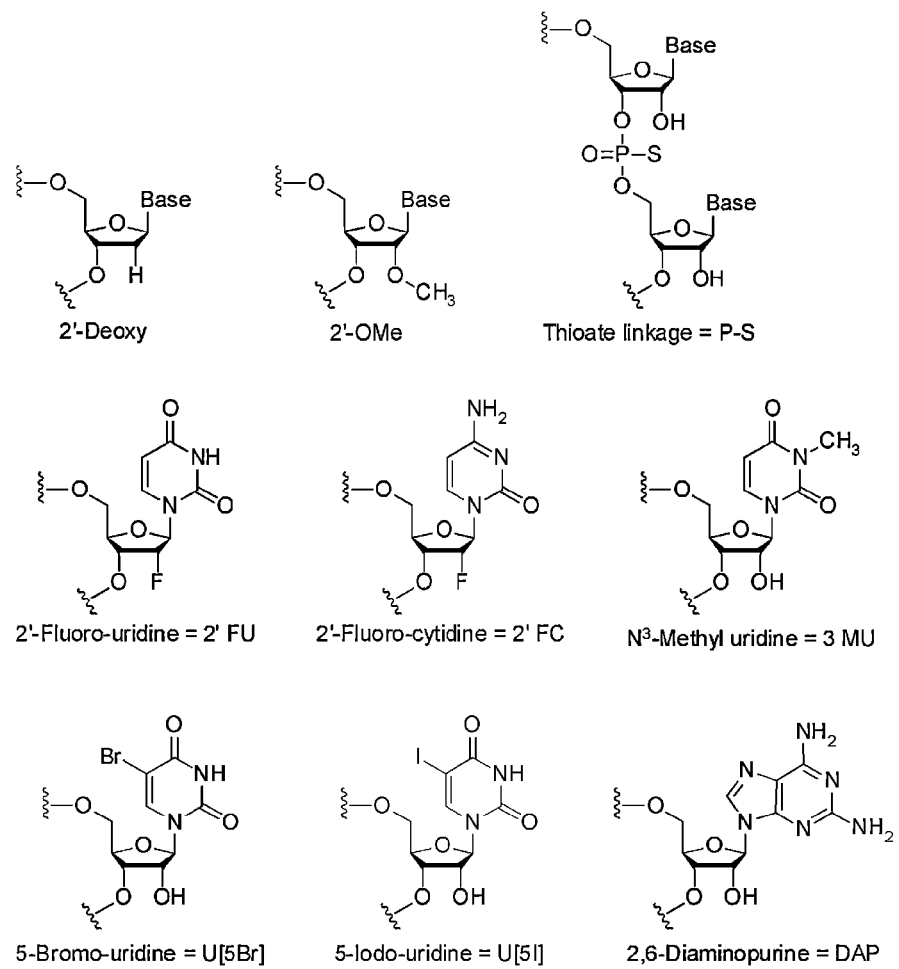
FIG. 1 shows some chemical modifications on siRNA.
Figure 2:
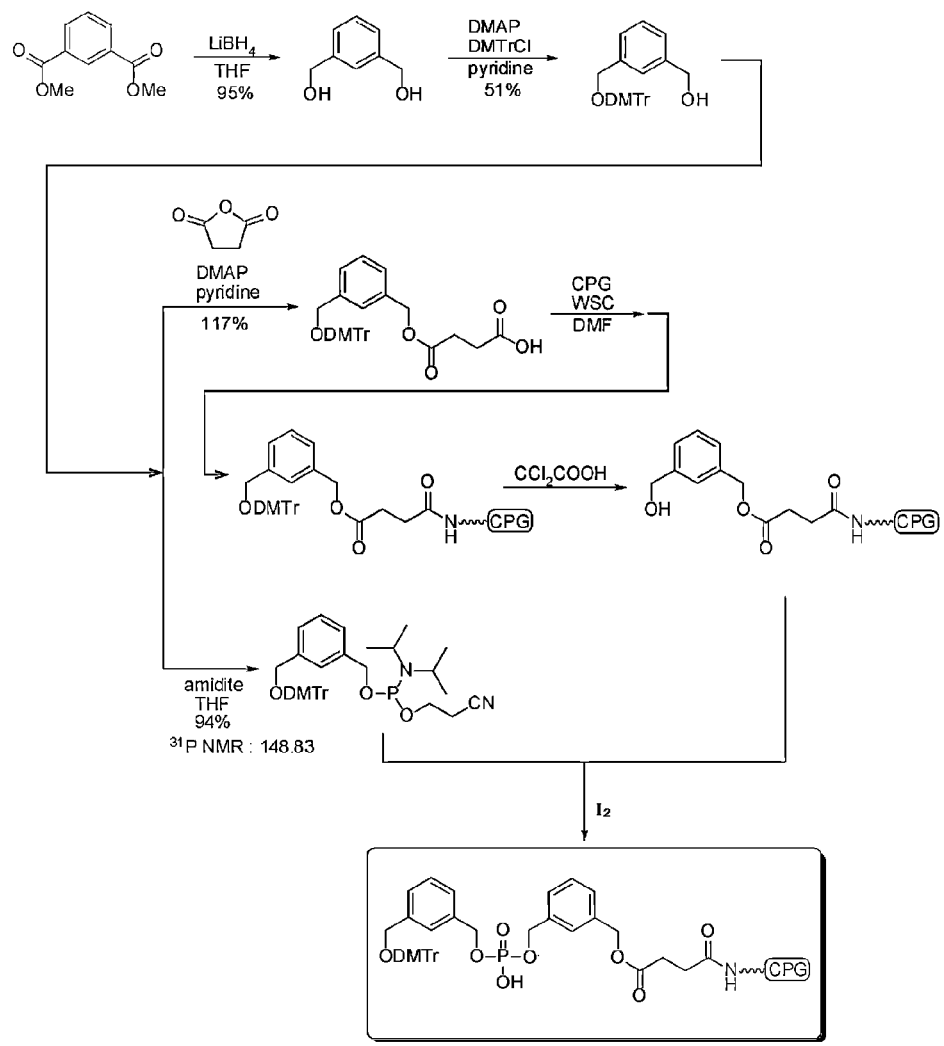
FIG. 2 shows the synthetic route of the modification carrier for synthesizing oligonucleotide derivative comprising two benzene structures linked via a phosphate diester bond and a CPG resin carrying them via a linker, described in Patent Document 1.
Figure 3:
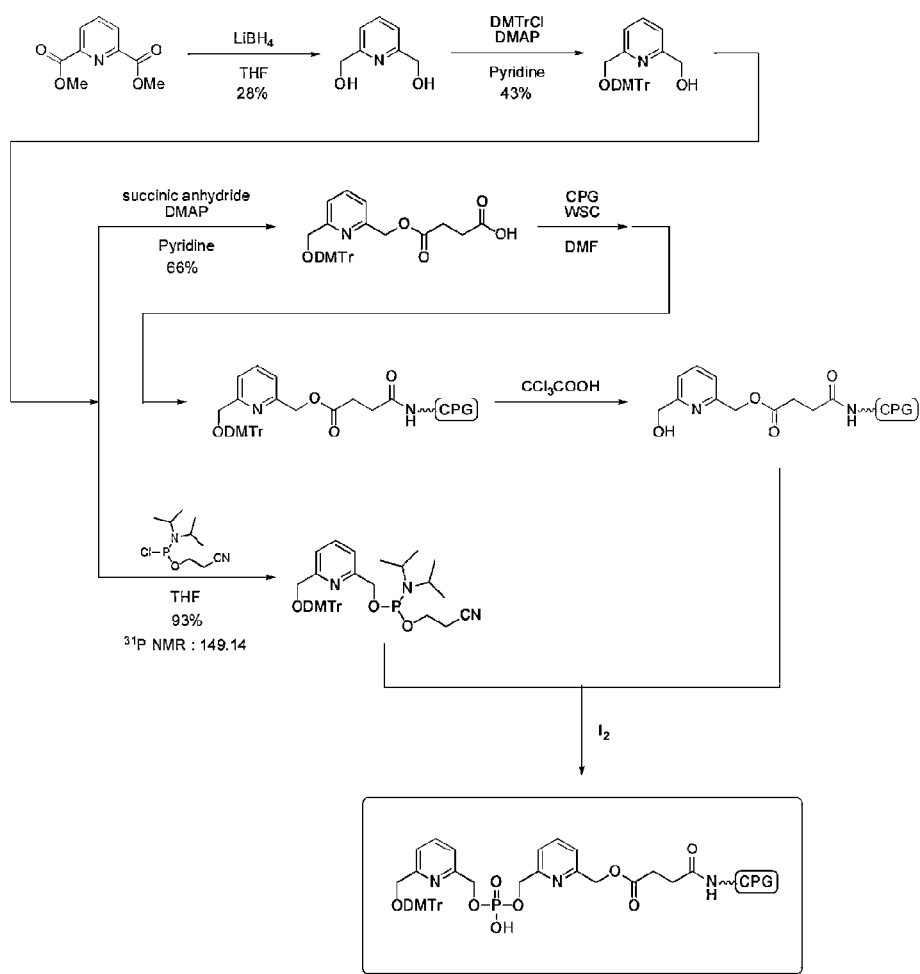
FIG. 3 shows the synthetic route of the modification carrier for synthesizing oligonucleotide derivative comprising two pyridine structures linked via a phosphate diester bond and a CPG resin carrying them via a linker, described in Patent Document 1.
Figure 4:
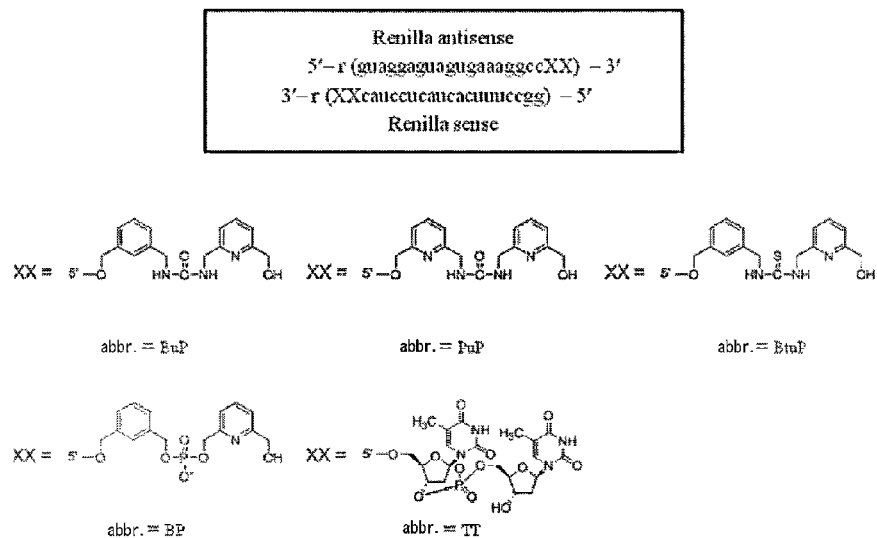
FIG. 4 shows sequences of oligonucleotides synthesized in Examples and Comparative Example.
Figure 5:
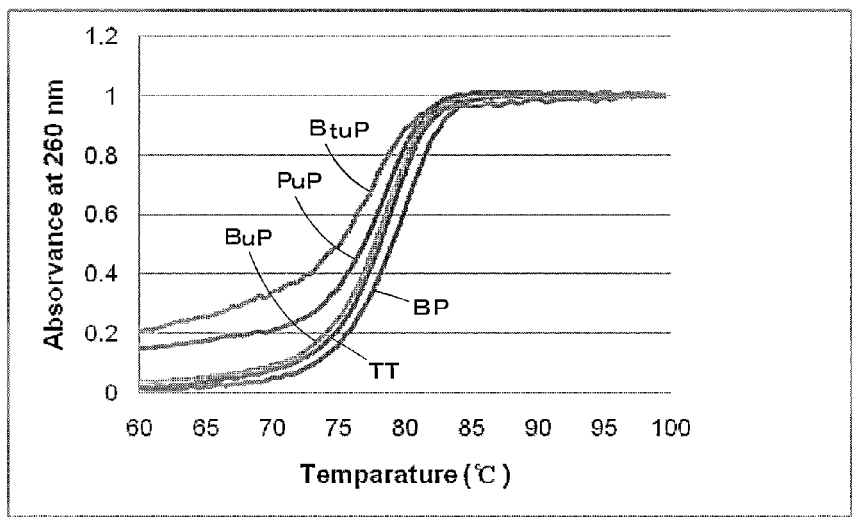
FIG. 5 shows a graph of thermal stability of siRNAs (BP, BuP, PuP, BtuP) of Examples and siRNA(TT) of Comparative Example.
Figure 6:
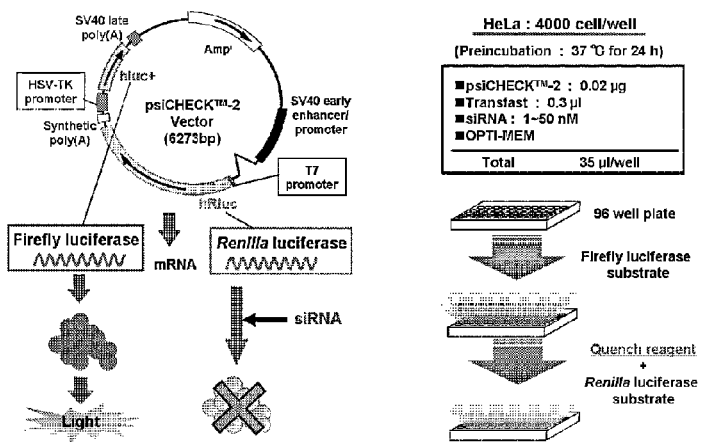
FIG. 6 shows a diagram of measurement of siRNA about effects to suppress expression of Renilla luciferase protein.
Figure 7:
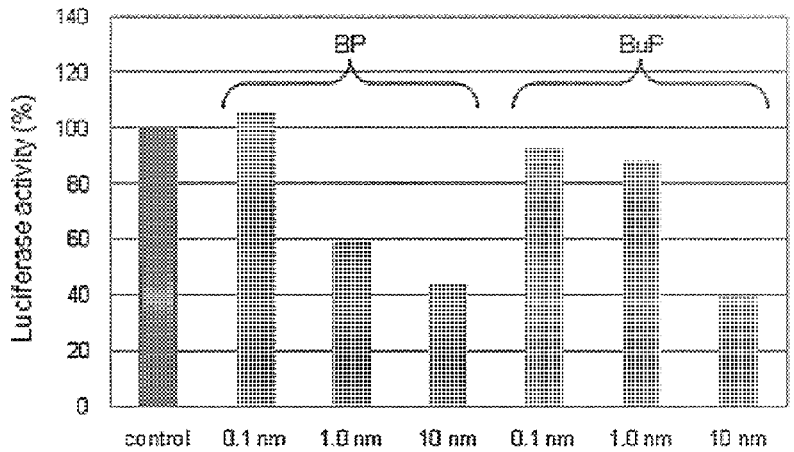
FIG. 7 shows a graph of effects of siRNA(BuP) of Example and siRNA(BP) of Comparative Example to suppress expression of Renilla luciferase protein, represented as proportions of luciferase activity calculated from luminescence intensities.
Figure 7:
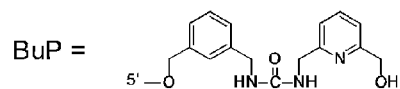
Figure 7:
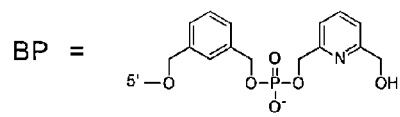
Figure 8:
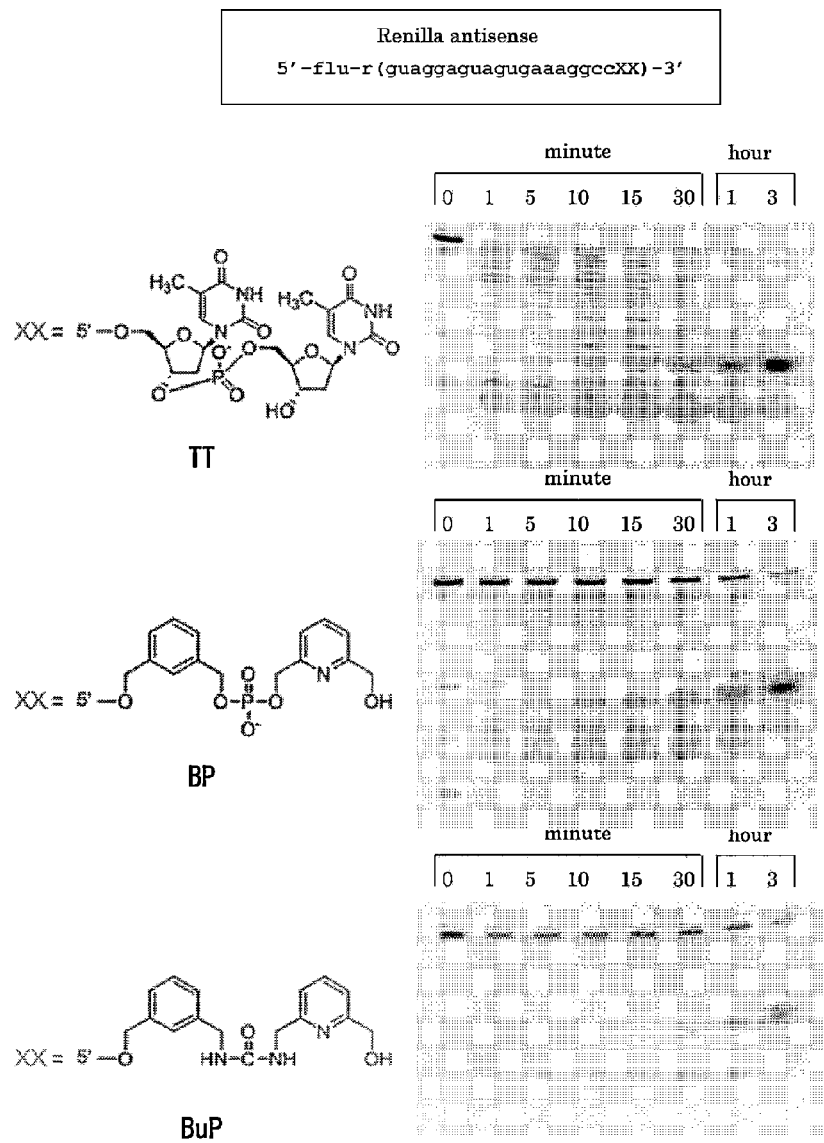
FIG. 8 shows results of electrophoresis determining respective degrees of nuclease resistance.
Figure 9:
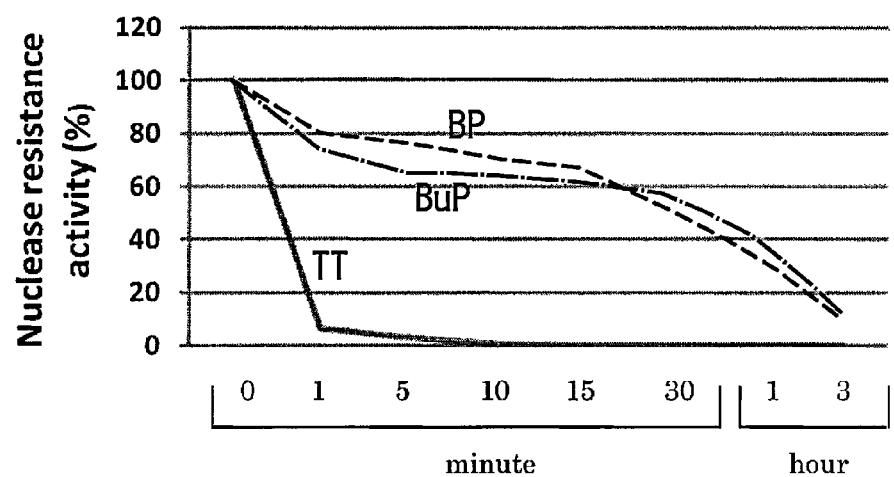
FIG. 9 shows a graph of nuclease resistance represented by the percentage of undegraded siRNA against the time.

The present invention provides useful tools in the field of medicine using nucleic acid oligomers, such as RNA drug discovery with potential in future development of personalized medicine.

[Sequence Listing]
PAF0020PCT Sequence Listing.txt

The invention claimed is:

1. An oligonucleotide derivative chemically modified at the 3'-end with a unit, wherein the unit is represented by the formula (a):

[formula 7]

(a)

wherein, $R_1$ to $R_6$ each independently represent hydrogen or a substituent other than hydrogen; $Z^1$ and $Z^2$ each independently represent CH or nitrogen; and X represents oxygen or sulfur.

2. The oligonucleotide derivative chemically modified at the 3'-end with a unit according to claim 1, wherein the unit is represented by the formula ($a_1$):

[formula 8]

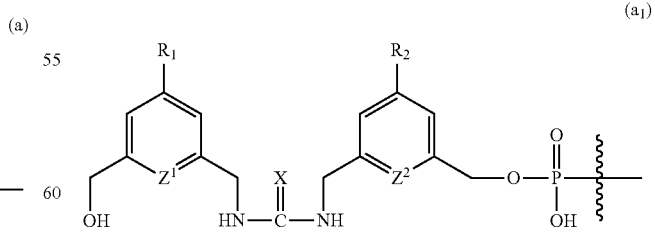

wherein, $R_1$ and $R_2$ each independently represent an alkyl, aryl, haloalkyl or halogen group; $Z^1$ and $Z^2$ each independently represent CH or nitrogen; and X represents oxygen or sulfur.

3. The oligonucleotide derivative chemically modified at the 3'-end with a unit according to claim 1, wherein the unit is represented by the formula (a₂):

[formula 9]

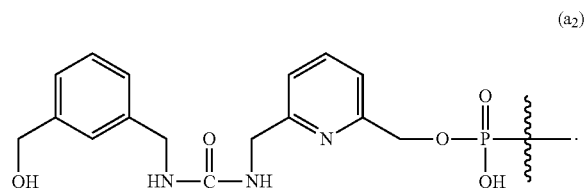

(a₂)

4. The oligonucleotide derivative according to any one of claims 1 to 3, wherein the oligonucleotide has a partial sequence of mRNA of a target gene or a complementary sequence thereof.

5. The oligonucleotide derivative according to claim 1, wherein a length of the oligonucleotide is not less than 10-mer to not more than 35-mer.

6. The oligonucleotide derivative according to claim 1, wherein the oligonucleotide is an oligoribonucleotide.

7. A construct comprising the oligonucleotide derivative according to claim 1, which is an oligonucleotide construct for regulating gene expression.

8. The construct according to claim 7, which is an oligonucleotide construct for regulating gene expression and selected from single- and double-strand DNAs, single- and double-strand RNAs, DNA/RNA chimeras, and DNA/RNA hybrids.

9. The construct according to claim 7 or 8, which is selected from antigene, antisense, aptamer, siRNA, miRNA, siRNA, and ribozyme.

10. A construct comprising the oligonucleotide derivative according to claim 7, which is an oligonucleotide construct for genetic diagnosis.

11. The construct according to claim 10, which is a probe or primer.

\* \* \* \* \*